(12) United States Patent
Fiolka et al.

(10) Patent No.: US 8,542,356 B2
(45) Date of Patent: Sep. 24, 2013

(54) MEASUREMENT METHOD AND MEASUREMENT SYSTEM FOR MEASURING BIREFRINGENCE

(75) Inventors: Damian Fiolka, Oberkochen (DE); Marc Rohe, Aalen (DE)

(73) Assignee: Carl Zeiss SMT GmbH, Oberkochen (DE)

( * ) Notice: Subject to any disclaimer, the term of this patent is extended or adjusted under 35 U.S.C. 154(b) by 0 days.

(21) Appl. No.: 13/237,000

(22) Filed: Sep. 20, 2011

(65) Prior Publication Data
US 2012/0092669 A1  Apr. 19, 2012

Related U.S. Application Data

(63) Continuation of application No. PCT/EP2010/001476, filed on Mar. 10, 2010.

(60) Provisional application No. 61/162,004, filed on Mar. 20, 2009.

(30) Foreign Application Priority Data

Mar. 20, 2009 (DE) .................. 10 2009 015 393

(51) Int. Cl.
*G01J 4/00* (2006.01)

(52) U.S. Cl.
USPC .......................................... 356/365; 356/364

(58) Field of Classification Search
USPC .................... 356/364, 365; 430/30
See application file for complete search history.

(56) References Cited

U.S. PATENT DOCUMENTS

| | | | |
|---|---|---|---|
| 4,886,361 A | 12/1989 | Furstenau | |
| 6,473,181 B1 | 10/2002 | Oakberg | |
| 6,697,157 B2 | 2/2004 | Wang et al. | |
| 6,697,199 B2 | 2/2004 | Gerhard et al. | |
| 7,955,765 B2 * | 6/2011 | Shinoda | 430/30 |
| 2003/0184749 A1 | 10/2003 | Yabu | |
| 2004/0008348 A1 | 1/2004 | Kishikawa et al. | |
| 2007/0171427 A1 | 7/2007 | Shiode | |
| 2009/0035671 A1 | 2/2009 | Shinoda | |
| 2009/0040522 A1 | 2/2009 | Otani et al. | |
| 2010/0182582 A1 | 7/2010 | Van De Kerkhof et al. | |

FOREIGN PATENT DOCUMENTS

| | | |
|---|---|---|
| DE | 10314185 A1 | 11/2003 |
| EP | 1847826 A1 | 10/2007 |
| GB | 2347496 A | 9/2000 |
| JP | 2001337035 A | 12/2001 |
| JP | 2004037137 A | 2/2004 |
| JP | 2007093289 A | 4/2007 |
| JP | 2007198896 A | 8/2007 |
| JP | 2008544507 A | 12/2008 |
| WO | 2007033710 A1 | 3/2007 |

* cited by examiner

*Primary Examiner* — Layla Lauchman
(74) *Attorney, Agent, or Firm* — Sughrue Mion, PLLC

(57) ABSTRACT

A method measuring the birefringence of an object. A measurement beam having a defined input polarization state is generated, the measurement beam being directed onto the object. Polarization properties of the measurement beam after interaction with the object are detected in order to generate polarization measurement values representing an output polarization state of the measurement beam after interaction with the object. The input polarization state of the measurement beam is modulated into at least four different measurement states in accordance with a periodic modulation function of an angle parameter $\alpha$, and the polarization measurement values associated with the at least four measurement states are processed to form a measurement function dependent on the angle parameter $\alpha$. A two-wave portion of the measurement function is determined and analysed in order to derive at least one birefringence parameter describing the birefringence, preferably by double Fourier transformation of the measurement function.

20 Claims, 14 Drawing Sheets

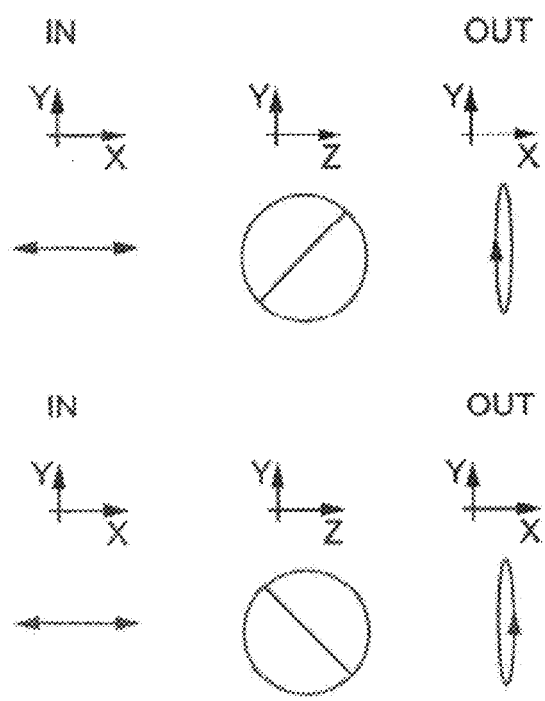
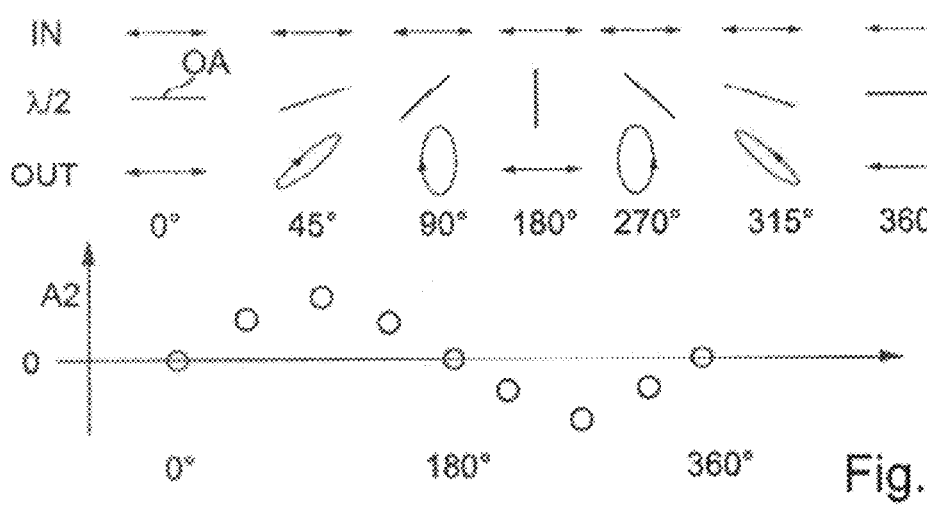
Fig. 4D
Fig. 4E

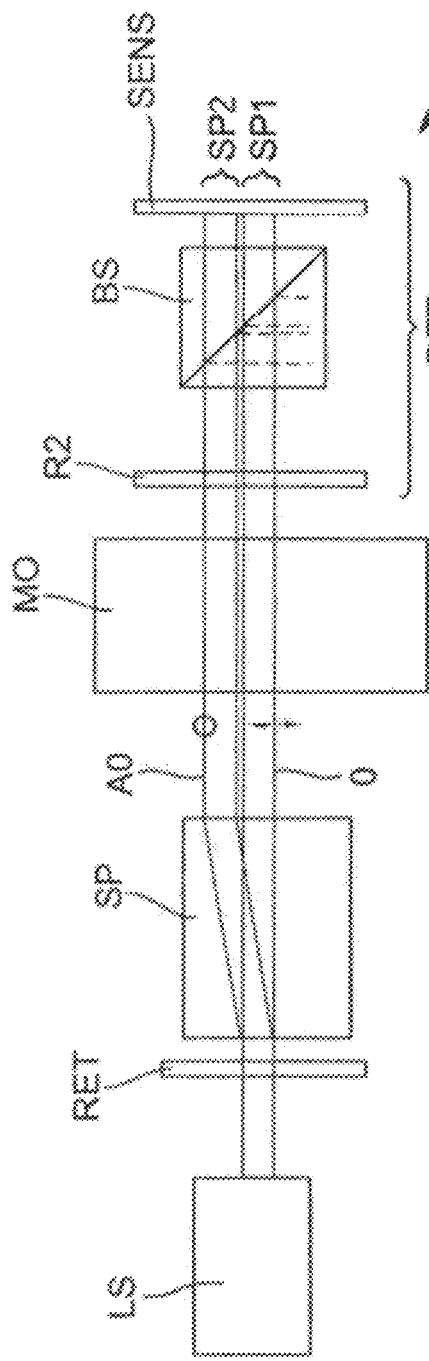
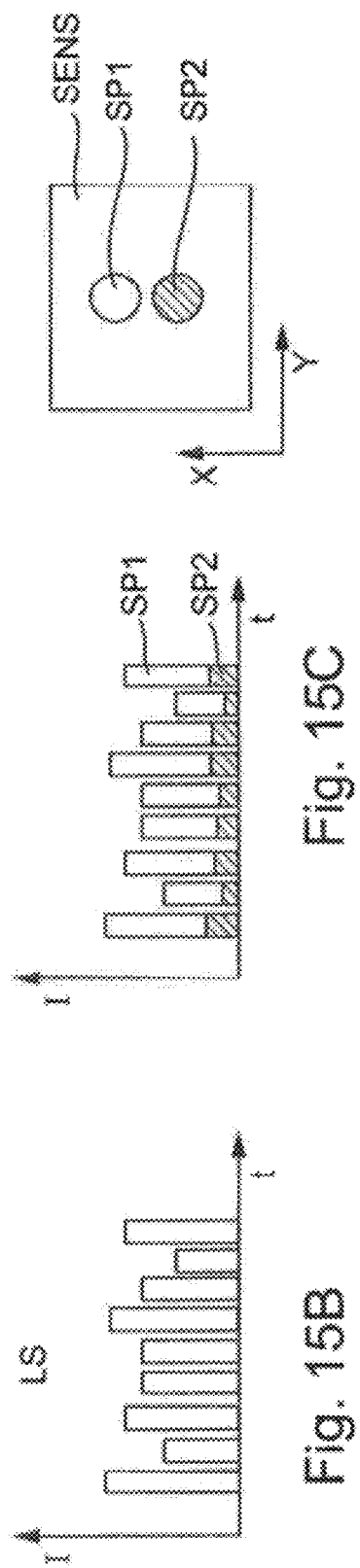
Fig. 15A
Fig. 15B
Fig. 15C

MEASUREMENT METHOD AND MEASUREMENT SYSTEM FOR MEASURING BIREFRINGENCE

CROSS REFERENCE TO RELATED APPLICATIONS

This application is a Continuation of International Application PCT/EP2010/001476, with an international filing date of Mar. 10, 2010, which was published under PCT Article 21(2) in English, which claims priority under 35 U.S.C. §119(a) to German Patent Application No 10 2009 015 393.4 filed on Mar. 20, 2009, and also to U.S. Provisional Patent Application 61/162,004 filed on Mar. 20, 2009. The entire contents of each of these three applications are incorporated into the present application by reference.

BACKGROUND OF THE INVENTION

1. Field of the Invention

The invention relates to a measurement method for measuring the birefringence of an optical measurement object, and to a measurement system suitable for carrying out the measurement method.

2. Description of the Related Prior Art

In many gases, liquids and stress-free amorphous solids, for example optical glasses, the speed of light is independent of the direction of propagation and of the polarization state of the light. Such optical media are referred to as optically isotropic. By contrast, if the optical properties of a material are dependent on the direction of propagation of the light, then the material is referred to as optically anisotropic. Many transparent crystalline materials are optically anisotropic. On account of the symmetry of their crystal lattice, they have at least one distinguished direction of symmetry, which is generally referred to as "optical crystal axis".

Many optically anisotropic materials exhibit birefringence. The term birefringence designates the property of optically anisotropic materials to split an incident light beam into two partial beams which are linearly polarized perpendicularly to one another and which propagate in different ways in the optically anisotropic material. The different propagation of light in anisotropic materials is substantially determined by the dependence of the speed of light on the direction of propagation and on the polarization state of the light. The propagation speed of one of the partial beams is independent of the direction of propagation. This partial beam is referred to as the "ordinary ray". By contrast, the propagation speed of the other partial beam is direction-dependent. This partial beam is referred to as the extraordinary ray. Associated with the different propagation speeds are correspondingly different refractive indices of the material for the different partial beams, where $n_o$ is the refractive index for the ordinary ray and $n_{eo}$ is the refractive index for the extraordinary ray. The birefringence based on the crystal structure of optical materials is referred to as intrinsic birefringence.

Optically isotropic materials can become birefringent as a result of external influences. Thus, by way of example, the birefringence induced by electric fields is used in the Kerr effect. In the case of intrinsically birefringent materials, the birefringent properties can change on account of external influences. In particular, mechanical stresses can induce birefringence, which is generally referred to as stress birefringence. Stress birefringence can be induced by internal stresses that result for example from the process for producing a crystal material. Furthermore, stress birefringence can be generated by external forces that arise e.g. in the course of mounting optical components in the mounts.

The birefringence is used as a desired property in the production of retardation elements (retarders), such as $\lambda/4$ plates or $\lambda/2$ plates, for example, or in the production of other polarization-optical components, in order to alter the polarization state of light in a defined manner.

On the other hand, in many demanding applications, for example in the field of microlithography, laser optics or astronomy, the birefringence of optical components is treated as an undesirable cause of error and endeavours are made to minimize the influence of birefringence on the optical properties of optical components or optical systems and/or to know it at least precisely enough that compensation is possible.

A precise knowledge of the extent of the birefringence, both in terms of the absolute value and in terms of the orientation of the birefringence, is important for controlling the birefringence. Therefore, there is a desire in the art for precise measurement methods for quantifying the birefringence.

Particularly stringent requirements made of the measurement accuracy and the capability of precisely determining even relatively weak birefringent effects exist in the field of optical systems for microlithography, which is used in particular in the production of large scale integrated semiconductor components and other finely structured components. In order to be able to produce ever finer structures with the aid of microlithography, the image-side numerical apertures of projection objectives are being increased ever further and ever shorter wavelengths are being used, in particular from the deep ultraviolet range (DUV). At wavelengths of less than 200 nm, only relatively few sufficiently transparent materials are available for producing transparent optical elements. They include primarily synthetic fused silica, which is sufficiently transparent down to 193 nm, and also some fluoride crystal materials, such as e.g. calcium fluoride or barium fluoride, which still exhibit sufficiently low absorption even at wavelengths of 157 nm and below. Calcium fluoride exhibits an intrinsic birefringence, i.e. a birefringence attributable to the crystal structure of the material, which, in addition to a possibly induced stress birefringence, can influence the polarization-optical behaviour of optical components composed of this material (cf. e.g. U.S. Pat. No. 6,697,199 B2 and literature citations indicated therein).

Each individual optical component exhibiting birefringence can make complex contributions to the polarization-optical behaviour of a system. Particularly in the field of microlithography, use is made of complex optical systems having a multiplicity of individual components which are often combined to form optical modules which perform specific functions within an overall optical system. In this case, it is generally desirable to know precisely both the birefringent properties of the overall system and the contributions of individual components or modules to the polarization-optical behaviour of the overall system.

In order to quantify the birefringence, measurement methods and measurement systems for measuring the birefringence of optical measurement objects are used, where the optical measurement object can be an individual optical component or a system comprising a plurality of optical components.

In the case of the measurement methods and measurement systems for quantifying the birefringence which are under consideration here, a measurement beam having a defined input polarization state is generated, said measurement beam being directed onto a measurement object, the input polarization state being the polarization state of the measurement beam directly before the measurement beam enters into the measurement object. After interaction of the measurement beam with the measurement object, polarization properties of the measurement beam are detected in order to generate polarization measurement values representing an output polarization state of the measurement beam, the output polarization state being the polarization state of the measurement beam after interaction with the measurement object.

The polarization measurement values are evaluated in order to determine at least one birefringence parameter representing the birefringence of the measurement object. In general, the absolute value and the orientation of the birefringence are determined. In this case, the absolute value of the birefringence represents the retardation—caused by the measurement object—between the two partial beams of the measurement beam which propagate at different propagation speeds in the material. The retardation between the two partial beams, which is also referred to as the optical path difference, is usually specified in nanometers or in fractions of the wavelength $\lambda$ of the measurement beam. Thus, by way of example, a $\lambda/4$ retarder at a measurement wavelength of 193 nm generates a path difference of 193/4 nm.

The orientation of the birefringence is defined by the orientation of the optical crystal axis of the birefringent material. If optically isotropic materials are involved which become birefringent as a result of an external influence, such as e.g. force action, then the orientation of the birefringence lies in the direction of the acting force. For the purposes of a measurement, the orientation of the birefringence can be expressed by angle indications relative to a defined reference direction of the measurement system.

A precise measurement presupposes that the input polarization state is set as precisely as possible and that the output polarization state is determined as precisely as possible. Errors arising when the input polarization state is generated and when the output polarization state is determined influence the measurement as measurement errors. These measurement error contributions should therefore be known or determinable in order to be able to be taken into account in the evaluation.

If, by way of example, the measurement is effected with the aid of a polarimeter or ellipsometer according to the Sérnarmont principle, then firstly a linearly polarized measurement beam is generated from the light from an unpolarized light source with the aid of a polarizer, said measurement beam entering into the measurement object. A birefringence within the measurement object generally leads to an elliptically polarized output polarization state. With the aid of a quarter-wave plate, linearly polarized light is generated again from the elliptically polarized light and its polarization angle can be determined with the aid of a rotatable analyzer arranged upstream of a light-sensitive detector.

U.S. Pat. No. 6,697,157 B2 and U.S. Pat. No. 6,473,181 B1 describe systems for measuring birefringence wherein a photoelastic modulator (PEM) is used for modulating polarized light, which is then radiated through a sample to be measured.

SUMMARY OF THE INVENTION

It is one object of the invention to provide a measurement method for measuring birefringence which permits a highly precise measurement of small values of birefringence. In particular, the measurement method is intended to have a measurement accuracy of less than 0.5 nm for small birefringence values.

It is a further object of the invention to provide a measurement method for measuring birefringence which is relatively insensitive to influences that generate measurement errors in the course of generating the input polarization state and in the course of evaluating the output polarization state.

It is a further object of the invention to provide a measurement method for measuring birefringence which makes it possible in a simple manner, using measurements on an optical measurement object having a plurality of optical components or component groups, to separate the contributions of the individual components or component groups to the birefringence of the overall measurement object.

It is a further object of the invention to provide a measurement method for measuring the birefringence of an optical measurement object which permits reliable separation between birefringence parameters of the measurement object which are to be measured and the disturbance variables—which impair the measurement—from components of the measurement system.

In order to achieve these and other objects, various formulations of the invention measurement methods and/or measurement systems as recited in various independent claims. Advantageous developments are specified in dependent claims. The wording of all the claims is incorporated by reference in the content of the description.

In the measurement method, the input polarization state of the measurement beam is modulated in accordance with a periodic modulation function of an angle parameter $\alpha$ in such a way that at least four different measurement states of the input polarization state are present for the measurement. The polarization measurement values associated with the at least four measurement states are processed to form a measurement function dependent on the angle parameter $\alpha$. The measurement function can be derived for example from an electrical measurement signal which is generated by the detector of a polarimeter and which is proportional to the intensity of the radiation impinging on the detector of the polarimeter.

The angle parameter $\alpha$ associated with the periodic modulation function of the input polarization state can for example be directly the rotation angle of a retardation plate arranged between a light source of the measurement system and the measurement object or be derived from said rotation angle. If, by way of example, a linearly polarized input polarization state in different orientations of the polarization direction is desired for the measurement, then these input polarization states can be generated by virtue of the fact that a polarization rotator for the rotation—controllable in a defined manner—of the polarization direction of the measurement beam, for example in the form of a rotatable half-wave plate, is arranged between a measurement light source for generating linearly polarized light and the measurement object. If, in the case of such an arrangement, a rotatable quarter-wave plate is used instead of a rotatable half-wave plate, then the input polarization state can be modulated in a predeterminable manner between linear polarization and circular polarization depending on the rotation angle of the quarter-wave plate. It is also possible to set the input polarization state with the aid of a combination of a half-wave plate and a quarter-wave plate and to define a corresponding angle parameter $\alpha$.

A two-wave portion of the measurement function is determined during the evaluation of the polarization measurement values. Said two-wave portion is analyzed in order to derive the at least one birefringence parameter.

The determination of a two-wave portion of the measurement function and the analysis of said portion in order to derive the at least one birefringence parameter are based on the insight that, under the given measurement conditions, the portion of the measurement signal which is attributed to the birefringence sought must have a significant two-wave characteristic, whereas measurement signal portions which are attributed to disturbance variables in the system generally do not have any significant two-wave undulation. Therefore, it is possible to identify, on the basis of the two-wave portion of a measurement signal, which portion of the measurement signal is causally attributed to the birefringence sought and which signal portions are based on disturbance variables that lead to measurement errors. If the two-wave portion of the measurement function is now determined and analyzed in a targeted manner during the evaluation, then the birefringence parameters derived from the analysis represent substantially exclusively the sought optical properties of the optical measurement object and represent possible disturbance contributions of the measurement system only to a negligibly small extent.

The expression "two-wave portion" designates in that context a two-fold symmetry in the angle space associated with the angle parameter $\alpha$, for example a two-fold rotational symmetry with respect to a rotation angle that is defined between 0° and 360°. Accordingly, those signal portions which have an angle distance of 180° relative to the angle parameter $\alpha$ contribute to the two-wave portion.

In a description of the problem with Fourier analysis, the two-wave undulation denotes the absolute value or the amplitude of that Fourier coefficient with which the sine portions and cosine portions, respectively, whose values are repeated after a period of 180° (that is to say double frequency) are weighted in a Fourier series. The significance of the "two-wave undulation" when determining the birefringence can be understood for example on the basis of the following considerations.

If birefringence occurs in a material, then an entering light beam is split into two partial beams which are in each case linearly polarized and the polarization directions of which are perpendicular to one another. The propagation speed of the light in one of the partial beams (ordinary ray) is direction-independent, whereas the propagation speed of the light of the other beam is dependent on the direction of propagation (extraordinary ray). The propagation of the ordinary and extraordinary rays can be explained with the aid of Huygens' principle. Huygens' principle states: every point on a wave surface is the starting point of new wavelets that are superimposed. A new wavefront is the envelope of the wavelets that are superimposed. The phase fronts of the wavelets in the case of the ordinary ray are spheres since the propagation speed is the same in each spatial direction. By contrast, the phase fronts of the wavelets of the extraordinary ray form ellipsoids of revolution since the propagation speed is direction-dependent. The ellipsoid of revolution, which has a two-fold or two-wave rotational symmetry relative to the direction of the light beam, contains the information about absolute value and orientation of the birefringence for each direction of incidence of a light beam. This information can be utilized by the determination and analysis of the two-wave portion of the measurement function directly for quantifying the birefringence.

The polarization measurement values associated with the at least four measurement states can be used as support values which determine the profile of the measurement function. The analysis of the measurement function, in preferred variants, makes use of the fact that every periodic function is composed of periodic, harmonic oscillations, that is to say sine and/or cosine functions of differing phase and amplitude and precisely defined frequency. This is utilized in the Fourier analysis, that is to say the decomposition of such a periodic function into a Fourier series.

In one variant of the measurement method, determining the two-wave portion of the measurement function comprises a double Fourier transformation of the measurement function. In this variant, the measurement values of the measurement function that are recorded during the measurement are analyzed with the aid of a double Fourier transformation or using two Fourier transformations carried out successively, a subsequent second Fourier transformation being applied to the result of a preceding first Fourier transformation. As a result, the birefringence parameters relevant to the birefringence become insensitive, in particular, to retardation errors in the setting of the different input polarization states and also insensitive to retardation errors that are introduced on the output side of the measurement object up to the recording of the measurement signal.

In one embodiment with double Fourier transformation, determining the two-wave portion of the measurement function comprises a first Fourier transformation of the measurement function in order to determine first Fourier coefficients $A0(\alpha)$ and $A2(\alpha)$, where $a0(\alpha)$ is an offset term describing an average value of non-periodic portions of the measurement function, and where $A2(\alpha)$ is a first two-wave undulation coefficient, which is proportional to the amplitude of the two-wave portion of the measurement function, and wherein determining the two-wave portion of the measurement function furthermore comprises a second Fourier transformation of the first Fourier coefficients $A0(\alpha)$ and $A2(\alpha)$ with respect to the angle parameter $\alpha$ in order to determine second Fourier coefficients $A0\_A01(\alpha)$, $A2\_A02(\alpha)$ and $B2\_A02(\alpha)$, where $A0\_A01(\alpha)$ is an offset term describing an average value of non-periodic portions of the offset term $A0(\alpha)$, $A2\_A02(\alpha)$ is a sine portion of the two-wave undulation of the first two-wave undulation coefficient $A2(\alpha)$, and $B2\_A02(\alpha)$ is a cosine portion of the two-wave undulation of the first two-wave undulation coefficient $A2(\alpha)$. The offset term $A0\_A01(\alpha)$ present after the second Fourier transformation can be utilized for an intensity normalization of the measurement result, whereby the measurement can be made insensitive to intensity fluctuations of the primary light source. The two-wave portions $A2\_A02(\alpha)$ and $B2\_A02(\alpha)$, which contain the information about the birefringence sought, follow from the second Fourier transformation of the first two-wave undulation coefficient $A2(\alpha)$.

In principle, the measurement method is not subject to any restrictions with regard to the at least four different measurement states for the input polarization state. The measurement states can lie at regular or irregular distances with respect to one another. The evaluation can be greatly simplified if the angle parameters $\alpha$ of the measurement function which are associated with the measurement states are equidistant with respect to one another. In this case, the Fourier transformation of the measurement function can be calculated using the so-called fast Fourier transformation (FFT), that is to say an algorithm in which the number of evaluation steps for determining the Fourier coefficients is significantly smaller than in more general cases of a Fourier transformation.

In one variant of the measurement method, a linearly polarized measurement beam having a polarization direction oriented parallel to the oscillation vector of the electric field is generated, said measurement beam being directed onto the measurement object, and the polarization direction of the measurement beam is rotated into at least four measurement orientations lying at predeterminable rotation angle distances with respect to one another. In this case, the measurement orientations correspond to the at least four different measurement states, while the rotation angle of the polarization direction corresponds to the angle parameter $\alpha$.

Preferably, the at least four measurement orientations lie at equidistant rotation angle distances with respect to one another, in order to enable an evaluation using fast Fourier transformation. In particular, $2^N$ where $N \geqq 2$ measurement orientations lying at equidistant rotation angle distances with respect to one another can be set, for example 4, 8, 16, 32 or 64 or more measurement orientations. Since each of the different measurement states of the input polarization corresponds to a support point for the measurement function to be evaluated, it is possible, by increasing the number of support points, to increase the accuracy in the determination of the measurement functions and thus also the measurement accuracy. On the other hand, by increasing the number of different input polarization states, the time expended on measurement and evaluation increases.

A calibration of the measurement system which can be carried out in a very simple manner is possible in the context of the measurement method. The analysis can be carried out such that the two-wave portions relevant to the birefringence are assembled additively and with exactly identical expressions from the birefringence parameters to be measured (in particular absolute value of the birefringence and orientation of the birefringence of the measurement object) and the disturbance variables generated by the measurement system, which include, in particular, birefringence contributions from retardation elements and analyzers of the measurement system. The simple additive relationship between the measurement variables of interest and the disturbance variables permits a reliable separation between the birefringence to be measured and the disturbance variables since, in this case, a birefringence portion generated by the measurement system itself (measurement system offset) can be determined by measurement without a measurement object, with an otherwise identical measurement method.

A simple addition of the relevant two-wave portions is possible after a linearization of the formulae describing the relationships with Taylor expansion. Therefore, the simple evaluation is suitable particularly for the exact determination of small birefringence values. The signal evaluation can become more complex if larger birefringence values are also intended to be determined with high accuracy.

Accordingly, in one method variant, a determination of a system portion of the birefringence parameters, which is attributed to components of the measurement system, is carried out with the following steps:
carrying out a measurement without a measurement object in the measurement beam path in such a way that the output polarization state to be analyzed corresponds to the input polarization state;
normalizing the sine portion $A2\_A02(\alpha)$ of the two-wave undulation of the first two-wave undulation coefficient $A2(\alpha)$ and the cosine portion $B2\_A02(\alpha)$ of the two-wave undulation of the first two-wave undulation coefficient $A2(\alpha)$ to the offset term $A0\_A01(\alpha)$ for the measurement with the measurement object in the measurement beam path in order to determine a normalized total measurement signal;
normalizing the sine portion $A2\_A02(\alpha)$ of the two-wave undulation of the first two-wave undulation coefficient $A2(\alpha)$ and the cosine portion $B2\_A02(\alpha)$ of the two-wave undulation of the first two-wave undulation coefficient $A2(\alpha)$ to the offset term $A0\_A01(\alpha)$ for the measurement without the measurement object in the measurement beam path in order to determine a normalized system portion of the total measurement signal;
subtracting the normalized system portion from the normalized total measurement signal.

The measurement method is suitable for the measurement of the birefringence of individual optical components or other individual samples and for the measurement on optical systems which contain at least two optical components through which radiation passes successively when the optical system is used as intended. The optical components can be individual optical elements, for example a lens, a transparent plate, a diffractive optical element, a diffractive or refractive raster arrangement with a multiplicity of individual elements through which radiation is to pass simultaneously, or others. Mirrors as measurement objects are also possible. By way of example, a birefringence induced by strain of dielectric layers can be measured here. A corresponding measurement set-up generally has a suitable beam deflection arrangement. An optical component can comprise a plurality of individual optical elements which are combined to form a functional group and, for example, can be jointly installed into an optical system or demounted, in the manner of an optical module. One variant of the measurement method makes it possible, in the case of an optical system constructed from a plurality of optical components, to measure the birefringence in the fully assembled state and in this case to separate the individual contributions of the individual optical components from one another. This method variant comprises the following steps:
carrying out a first measurement, in which the measurement beam passes firstly through the first optical component and then through the second optical component; and
carrying out a second measurement, in which a polarization state of the measurement beam is rotated by 90° relative to the polarization state in the first measurement after said measurement beam passes through the first optical component and before it enters into the second optical component.

In the first measurement, generally the output polarization state after passage through the first component serves directly as the input polarization state for the passage through the second optical component, while in the second measurement the output polarization state after passage through the first optical component is altered by the generation of a $\lambda/2$ retardation before entry into the second optical component. The output polarization state of the measurement beam after passage through the second optical component is analyzed and evaluated in the same way in both measurements in order to obtain a first measurement result (of the first measurement) and a second measurement result (of the second measurement). The contribution of the first optical component through which radiation first passes is found again in an identical manner in both measurement results. In contrast to this, the second optical component makes different contributions to the measurement results since the measurement beam passes through the second optical component with two different polarization states of said measurement beam.

Since the contribution of the first optical component is the same in both measurement results, the contribution of the first optical component to the measurement results can be eliminated by forming a difference between the first measurement result and the second measurement result, such that a difference between the measurement results contains only the birefringence portions of the second optical component and of the measurement apparatus. By contrast, the sum of the measurement results, that is to say the sum of the two-wave undulations of the first measurement and of the second measurement, contains only the information about the birefringence of the second optical component since, on account of the 90° rotation of the polarization state that is introduced between the optical components, the contributions of the second optical component and also the system portion cancel one another out at least to a first approximation.

In the mathematical description of birefringent elements or of manipulations of the polarization, use is generally made of matrices (Jones matrices or Müller matrices) which are to be treated multiplicatively. By virtue of the mathematical expressions that describe the birefringence being linearized and suitably combined, the further processing can be replaced by an additive method. The latter permits the addition of the birefringence portions of the first optical component and of the second optical component.

Since, in order to carry out the two different measurements, it is merely necessary to introduce a suitable polarization rotator between the first component and the second component or to remove it from this intermediate position, a measurement of the birefringence contributions of the first and second optical components is also possible when the latter have already been fixedly assembled in that relative configuration in which they are used in the context of an overall optical system. Consequently, it is not necessary to disassemble a complex optical system in order to determine the birefringence portions of individual optical components of said optical system.

A further advantage that arises is that the birefringence contribution of the first optical component can be determined exactly after the two measurements have been carried out, even without prior calibration of the measurement device portion, since the latter vanishes to a first approximation in the course of the difference formation.

In an analogous manner, it is also possible to obtain exact measurement results without calibrating the measurement apparatus beforehand. As already explained, the determination of the sum of the two-wave undulations from the first measurement and the second measurement, owing to the 90° rotation of the polarization state that is introduced in one of the measurements relative to the first measurement, has the effect that the system portion can be eliminated from the measurement signal. This can be understood clearly since it influences the measurement result positively in the case of the first measurement and with the opposite sign in the case of the second measurement (with the polarization state rotated by 90°). The summation thus leads to an elimination of the system portion. This effect can be utilized to a first approximation "calibration-free" measurement of the entire measurement optics. A corresponding method variant comprises the following steps:

carrying out a first measurement, in which the measurement beam enters into the detector side of the measurement system after passing through the measurement object without further polarization alteration;

carrying out a second measurement, in which the polarization state of the measurement beam is rotated by 90° after the measurement beam has passed through the measurement object and before the measurement beam enters into a detector-side part of the measurement system;

jointly evaluating the first measurement and the second measurement.

In general, the birefringence contributions of different components or assemblies in the measurement beam path can be separated from one another in some method variants with the aid of the following method steps: carrying out a first measurement in order to determine first birefringence parameters;

carrying out a second measurement in order to determine second birefringence parameters, wherein, during the second measurement, the polarization state of the measurement beam is rotated by 90° relative to the polarization state of the measurement beam of the first measurement by introducing a polarization rotator into the measurement beam or by removing a polarization rotator from the measurement beam in a polarization rotation section with respect to the corresponding polarization state of the measurement beam during the first measurement;

jointly evaluating the first birefringence parameters and the second birefringence parameters.

The joint evaluation can comprise determining a sum between the two-wave portions of the measurement function of the first measurement and second measurement and/or determining a difference between the two-wave portions of the measurement function of the first and the second measurements.

The result of the summation contains in each case only the birefringence contributions of all the optical elements in the measurement beam path between the measurement light source and the polarization rotation section since the contributions of all the optical components which are situated downstream of the polarization rotation section in the transmission direction cancel one another out to a first approximation in the course of the summation.

By contrast, the result of the difference formation contains to a first approximation only the birefringence portions of those optical components and components which are situated between the polarization rotation section and the detector side of the measurement system since the portion of the elements and components lying between light source and polarization rotation section is ideally identical in both measurements and therefore vanishes as a result of the difference formation.

If the polarization rotation section is situated between the measurement object and a detector-side component of the measurement system, the system portion of the measurement result can be eliminated by the summation, for example, such that a separate calibration of the measurement apparatus can be obviated.

If the measurement object contains a plurality of optical components arranged one behind another in the transmission direction and the polarization rotation section lies between a first optical component and a second optical component, then the birefringence contributions of the first optical component and of the second optical component can be separated from one another.

In the context of a measurement cycle, at different locations of the measurement beam path, one or a plurality of 90° polarization rotators can optionally be introduced into the beam path or removed from the measurement beam path in order to obtain exact measurement data (a) concerning the individual contributions of different components or component groups of the measurement object and also (b) concerning the contributions of the measurement system using a small number of measurements with 90° polarization rotators optionally introduced or removed.

A 90° polarization rotator can have for example a plate composed of optically active (circularly birefringent) material, e.g. composed of crystalline quartz ($SiO_2$). With such elements, even in the case of a large optically usable diameter, for example optical diameters of 100 mm or more, or 150 mm or more, or 200 mm or more, the desired polarization rotations can be set very exactly since the mechanical tolerances for obtaining a desired 90° rotation of the polarization state can lie in the micrometers range in order to achieve rotation accuracies of less than 1°. Polarization rotators which are mechanically stable and also suitable for larger diameters can also be produced from intrinsically birefringent crystal material, for example calcium fluoride or barium fluoride, in which a crystallographic <110> direction is oriented substantially parallel to the transmission direction. Since the absolute values of the intrinsic birefringence are relatively small in the case of these materials, such elements can have a relatively large thickness, which is favourable for the mechanical stability and the manufacturing accuracy. Zeroth-order retardation elements are advantageous here in order to obtain a largest possible angle tolerance. It is also possible for a 90° polarization rotator to have two low-order $\lambda/2$ plates oriented at 45° relative to one another. In this case, the optical crystal axes of the retardation plates rotated relative to one another are substantially perpendicular to the transmission direction or perpendicular to the optical axis of the measurement system.

The measurement accuracy of the measurement method can be impaired by intensity fluctuations of the measurement light used. In order to minimize the influence of intensity fluctuations of the measurement light source on the accuracy of the measurement, some variants of the method involve carrying out time-dependent detection of a reference intensity signal, which is proportional to the intensity of the measurement light emitted by a measurement light source, and normalizing the polarization measurement signal to the reference intensity signal in order to determine normalized polarization measurement signals. In this case, the term "polarization measurement signal" designates the useful signal which is determined by the measurement and from which the measurement function to be analyzed is derived. In general, this is an electrical signal which is proportional to the intensity of the measurement radiation impinging on an optoelectronic transducer.

For this purpose, provision may be made, for example, for splitting the measurement beam whose polarization properties are intended to be determined, using a polarization beam splitter or some other, substantially polarization-maintaining and polarization-selectively reflective element, such that it is possible to measure a continuous (non-reflected) portion with a polarization measuring optic and a connected sensor. The reflected part can be directed in a reference branch onto a second sensor, which serves as a reference sensor and generates a reference intensity signal which is proportional to the intensity of the measurement light emitted by the measurement light source. Said reference intensity signal can serve for energy referencing, in order to reduce the measurement errors attributed to intensity fluctuation of the measurement light source. As a result of the polarization-selective splitting of the measurement radiation before the measurement, the polarization state which is actually intended to be measured can be influenced. Therefore, if appropriate, a special calibration is necessary for this effect. Furthermore, alongside the measurement sensor, a further sensor is required for detecting the reference intensity signal.

One particular variant of the method avoids these disadvantages. This method variant comprises the following steps: splitting the measurement beam into a linearly polarized first partial beam having a first intensity and a second partial beam having a second intensity, said second partial beam being linearly polarized perpendicularly to the first partial beam; guiding the first partial beam and the second partial beam along polarization-optically substantially identical beam paths onto spatially separate first and second sensor zones of a sensor area of an intensity sensor in order to generate a first intensity signal proportional to the first intensity and a second intensity signal proportional to the second intensity; and processing the first intensity signal and the second intensity signal to form a combination signal.

In this case, the expression "along polarization-optically substantially identical beam paths" relates to the polarization-optical equivalence of the beam paths. Beam paths are "polarization-optically substantially identical" in this sense if the partial beams, along their respective beam paths, experience in each case no or in any event approximately the same or mutually corresponding changes in the polarization as a result of possible polarization-influencing elements in the system. The beam paths can be very close to one another geometrically, such that partial beams pass through e.g. substantially the same material volumes. The beam paths can also be different geometrically, in which case e.g. one of the partial beams can be singularly or multiply folded at mirror surfaces. One partial beam may, if appropriate, also be phase-retarded relative to the other partial beam by exactly one wavelength or an integer multiple of the wavelength.

The measurement beam, the intensity of which possibly fluctuates, can therefore be split in such a way that both partial beams impinge simultaneously on different, spatially mutually separate locations or zones of one and the same sensor and are evaluated there with regard to their intensity during a polarization measurement. The two partial beams can be guided between the splitting location and the sensor area in such a way that they experience no or in any event approximately the same changes in the polarization as a result of possible polarization-influencing elements in the system, such that they arrive at the detector side of the measurement system still in a manner polarized approximately orthogonally with respect to one another. Under these conditions, the sum of the first intensity signal and the second intensity signal at any point in time is proportional to the input-side intensity of the measurement beam emitted by the measurement light source and can thus be utilized as a reference intensity signal. Accordingly, one method variant comprises forming an intensity reference signal using the sum of the first intensity signal and the second intensity signal.

As an alternative, formation of a combination signal can be carried out using a ratio between the first intensity signal and the second intensity signal. This is because if the orientation of a birefringent element utilized for splitting the measurement beam with respect to a coordinate system of the measurement object is known, then the polarization portions in the direction of the polarization of the ordinary ray and of the extraordinary ray can be deduced from the ratio of the two intensities in the first and second sensor zones.

The measurement beam can be split into two partial beams (ordinary ray and extraordinary ray) polarized perpendicularly to one another by a birefringent element, for example. It is also possible to split the measurement beam into a partial beam having p-polarization and a partial beam having s-polarization with the aid of a polarization-selectively acting polarization beam splitter and then to direct the two partial beams onto different, non-overlapping regions of the same sensor area.

The measurement beam can be split upstream or downstream of the measurement object in the light propagation direction. It is possible to accommodate a beam splitting element (e.g. a birefringent element or a polarization beam splitter) in direct proximity to the sensor area of a detector unit within the detector unit.

The methods and devices for energy referencing that have been described here and are explained in greater detail below in connection with various embodiments can advantageously be utilized in embodiments of measurement methods and measurement systems according to the invention. However, they can also be utilized independently of said measurement methods and measurement systems in other measurement methods and measurement systems, for example in other polarization measurement methods and polarization measurement systems, which need not necessarily serve for determining the birefringence. By way of example, the energy referencing can be used in polarization measurement methods and systems which are designed for measuring the polarization-dependent transmission (diattenuation).

The above and further features emerge not only from the claims but also from the description and the drawings, wherein the individual features can be realized in each case for themselves or as a plurality in the form of sub-combinations in embodiments of the invention and in other fields and can constitute advantageous and inherently protectable embodiments.

BRIEF DESCRIPTION OF THE DRAWINGS

FIG. 15 shows in 15A schematically the construction and the function of some components of the measurement system for monitoring intensity fluctuations of the primary light source for the purpose of energy referencing, in 15B the temporal fluctuation of the intensity of the primary light source, and in 15C the temporal fluctuations of the intensities for two illumination spots which are adjacent to one another and which are generated by partial beams polarized orthogonally with respect to one another;

DETAILED DESCRIPTION OF VARIOUS PREFERRED EMBODIMENTS

Figure 1:
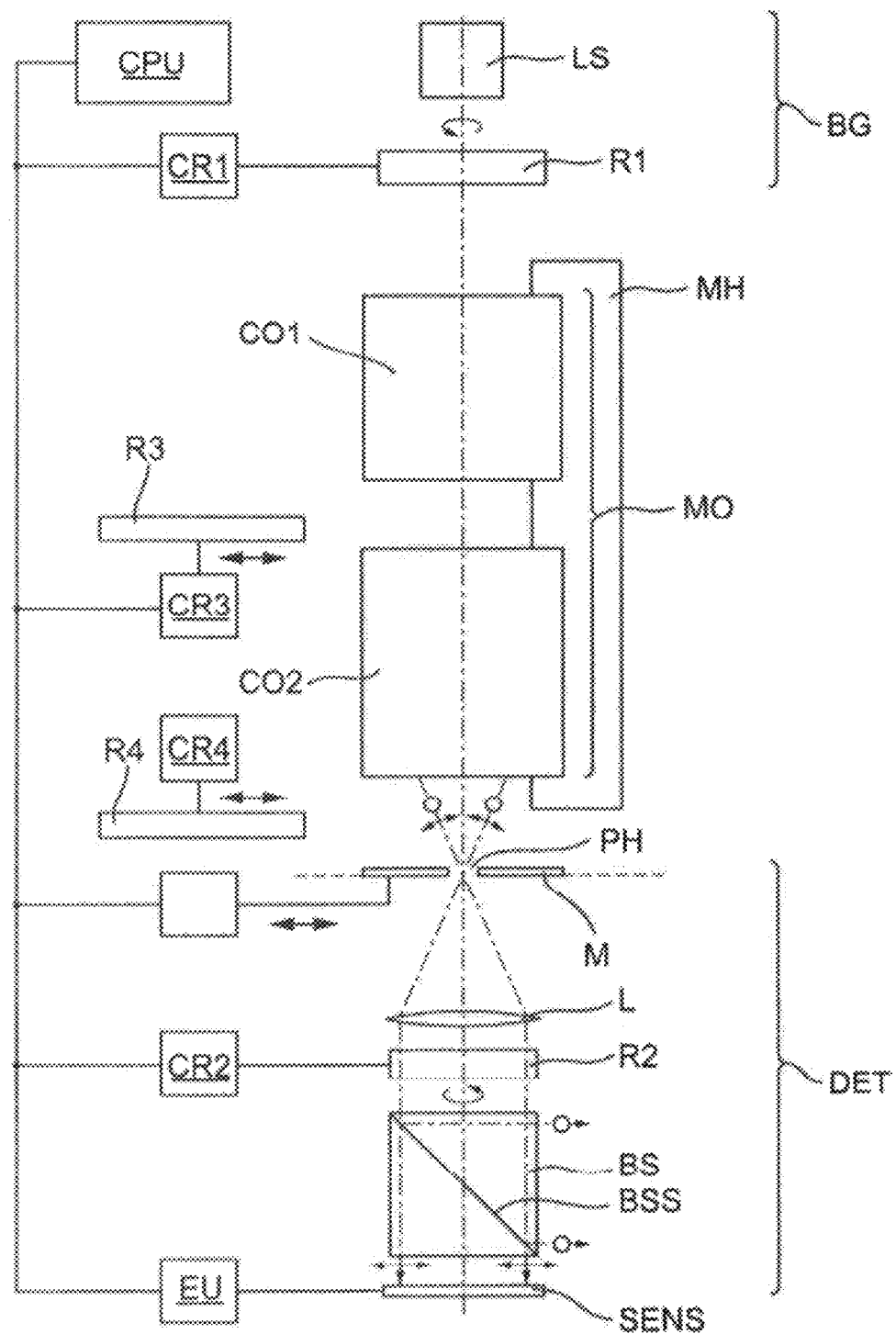
FIG. 1 shows an embodiment of a measurement system for measuring the birefringence of a measurement object.

FIG. 1 shows an embodiment of a measurement system MS for measuring the birefringence of a measurement object MO, which in the case of the example is constructed in multipartite fashion and comprises a first component CO1 and also a second component CO2 arranged downstream thereof in the transmission direction, which are jointly held in a measurement object holding device MH in the manner in which they are also arranged relative to one another when an optical system containing the two components is used as intended. The measurement system comprises a beam generating unit BG for generating a measurement beam which is directed onto the measurement object and which is intended to have a defined input polarization state upon entering into the measurement object, and also a detector unit DET for detecting polarization properties of the measurement beam after passage through the measurement object or upon entry into the detector unit. If a measurement object is situated in the measurement beam path, the detector unit generates, during the measurement, polarization measurement values representing the output polarization state of the measurement beam after passage through the measurement object. An evaluation unit EU connected to the detector unit serves for evaluating the polarization measurement values and for determining at least one birefringence parameter representing the birefringence of the measurement object. In the case of the example, the birefringence parameters determined permit an exact determination of the extent or the absolute value of the birefringence generated by the measurement object, and also of the orientation of said birefringence relative to a reference coordinate system. The evaluation unit EU can be integrated into the control unit CU of the measurement system.

The beam generating unit BG comprises a measurement light source LS in the form of an ArF excimer laser which emits a linearly polarized laser beam having a nominal wavelength of approximately λ=193 nm, and also a first polarization rotator R1 in the form of a half-wave plate (λ/2 plate), which can be rotated about the optical axis OA of the measurement system in defined rotation angle steps using a first control device CR1. With the aid of the combination of measurement light source LS and first polarization rotator R1, it is possible to generate a linearly polarized measurement beam having a polarization direction oriented parallel to the oscillation vector of the electric field, the orientation of which polarization direction can be brought into any desired rotation angle position by rotation of the polarization rotator R1 with high accuracy. The term "polarization rotator" in association with the half-wave plate R1 generally denotes an optical element that rotates the polarization direction.

Furthermore, the measurement system of the embodiment comprises a second polarization rotator R3, which is designed as a 90° polarization rotator for rotating the polarization state of the light passing through by 90°. The 90° polarization rotator R3 has a 90° rotator plate composed of optically active material, which can optionally be introduced into the measurement beam path or removed from the measurement beam path with the aid of an assigned control device CR3. This 90° polarization rotator is arranged in the region of the measurement object holding device and can be inserted in particular between two components CO1 and CO2 of a measurement object in order to enable measurements of the birefringence with different measurement configurations. Details will be explained more specifically further below.

Furthermore, the measurement system of the embodiment comprises a third polarization rotator R4 in the form of a 90° rotator plate composed of optically active material, which can optionally be introduced into the measurement beam path or be removed from the measurement beam path directly upstream of the detector unit with the aid of an assigned control unit CR4. This 90° polarization rotator can be used in particular during the calibration of the measurement system, which will be explained in even greater detail further below.

The detector unit DET has a light-opaque mask M having a small region trans-parent to the measurement light in the form of a "pinhole" PH, the diameter of which is significantly greater than the operating wavelength and can lie for example in the range of 100 μm to 300 μm. The pinhole PH forms the entrance opening of the detector unit. The mask M is fitted in the front focal plane of a positive lens L, which can consist of one or more individual lenses. Situated in the back focal plane of this lens is a spatially resolving sensor SENS in the form of a CCD sensor, which is able to generate sensor signals which are proportional to the intensity of the radiation impinging on the respective location of the sensor area. Arranged between the lens L and the sensor is a rotatable retardation element R2 in the form of a quarter-wave plate (λ/4 plate), which, with the aid of a control unit CR2 for the retardation element, can be rotated about the optical axis of the measurement system and be brought into defined rotation angle positions in the process. Situated between the λ/4 retardation element R2 and the sensor is a polarization beam splitter BS having a polarization-selective beam splitter surface BSS lying at 45° with respect to the optical axis. In this arrangement, the polarization beam splitter functions as an analyzer. The latter transmits to the sensor SENS only those portions of the polarized radiation—collimated by the lens L and altered by the retardation element R2—which are p-polarized with respect to a plane of incidence spanned by the direction of incidence and a surface normal to the beam splitter surface, that is to say whose electric field vector oscillators parallel to said plane of incidence. By contrast, the portions with s-polarization (oscillation direction of the electric field vector perpendicular to the plane of incidence) are reflected to the side.

The detector unit DET can be displaced as a whole to predetermined positions in a plane perpendicularly to the optical axis OA of the measurement object, such that the pinhole PH can be arranged at different locations relative to the optical axis of the measurement object, in order in this way to enable a spatially resolving measurement of the polarization state. The detector unit furthermore permits an angularly resolving measurement of the polarization state with a high angular resolution of 1 mrad or better for all the measurement points which can be defined by the positioning of the pinhole. As an alternative, pyroelectric sensors or photodiodes can also be used as detectors.

To afford a better understanding of important aspects of the invention, the functioning of a polarization measurement with the aid of such a detector arrangement will be explained in greater detail below. The polarization of the light which passes through the pinhole and is collimated by the lens L is changed in a targeted manner by the rotatable λ/4 plate. The analyzer, embodied here as a polarization beam splitter, transmits only p-polarization to the sensor. Depending on the rotational position of the λ/4 plate, an intensity signal arises on the sensor, and the polarization state of the light bundle incident in the detector unit can be determined unambiguously from said intensity signal.

Figure 2A:
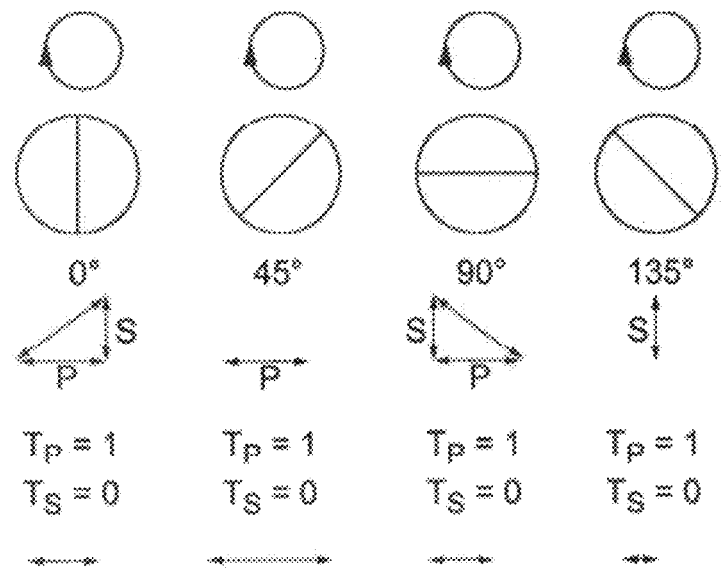
FIG. 2 shows in 2A schematic illustrations of polarization states within the detector unit and in 2B the relative intensity profile as a function of the rotational position of the λ/4 plate of the detector unit in the case of a full rotation of the λ/4 plate in the case of a circularly polarized input polarization state.
Figure 2B:
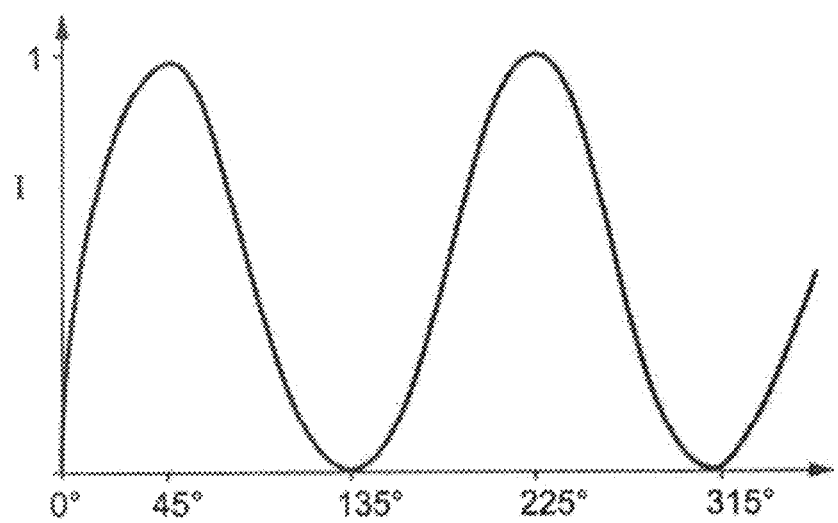

For circularly polarized input light, the sensor registers the relative intensity profile shown in FIG. 2B as a function of the rotational position of the λ/4 plate after a 360° rotation. Assuming an ideal λ/4 retardation, a pure two-wave undulation of the measurement signal arises, that is to say a measurement signal having a rotation angle periodicity of 180°. This symmetry can also be referred to as two-wave or two-fold azimuthal symmetry. This can be understood by referring to FIG. 2A. FIG. 2A shows, in the four sub-figures adjacent to one another, in each case at the top the circularly polarized input polarization state, underneath that the rotational position of the λ/4 plate, symbolized by the orientation of the optical crystal axis, underneath that the polarization of the beam after passage through the λ/4 plate, and underneath that those polarization components which the analyzer (beam splitter cube) transmits to the sensor. In this case, Tp and Ts are the respective transmissions of the analyzer for p-polarization and s-polarization.

The λ/4 retardation element converts circularly polarized light into linearly polarized light. The orientation of the linearly polarized light is dependent on the orientation of the optical crystal axis of the retardation element. At the 45° position of the retardation element, only p-polarization is present at the exit of the retardation element, which generates a maximum signal at the sensor. At the 135° position angularly offset by 90°, by contrast, the retardation element transmits only s-polarization, which is completely reflected by the analyzer, with the result that no intensity signal arises at the sensor. Corresponding relations arise at the angle positions displaced by 180°, with the result that a pure two-wave undulation of the measurement signal arises in the course of a full rotation of the retardation element.

Figure 3A:
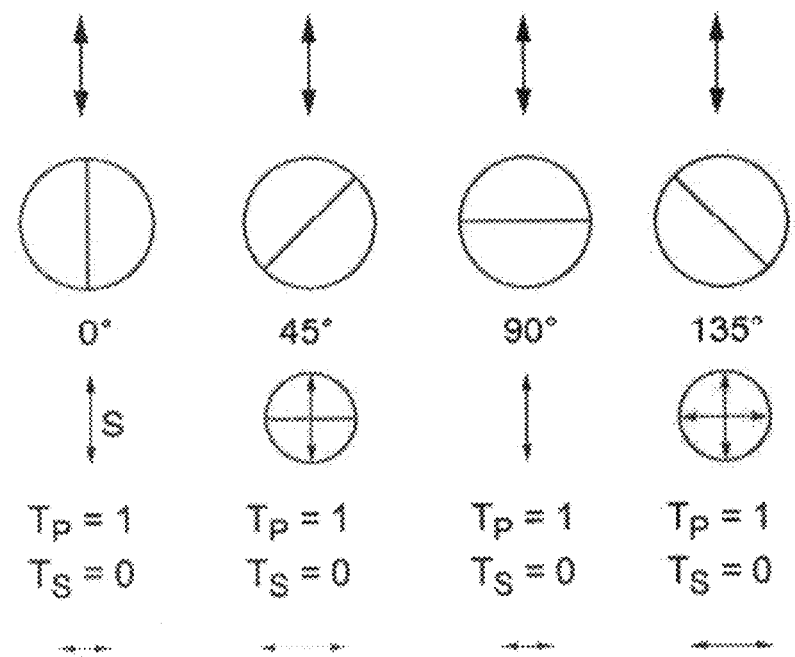
FIG. 3 shows in 3A schematic illustrations of polarization states within the detector unit and in 2B the relative intensity profile as a function of the rotational position of the λ/4 plate of the detector unit in the case of a full rotation of the λ/4 plate in the case of a linearly polarized input polarization state.
Figure 3B:
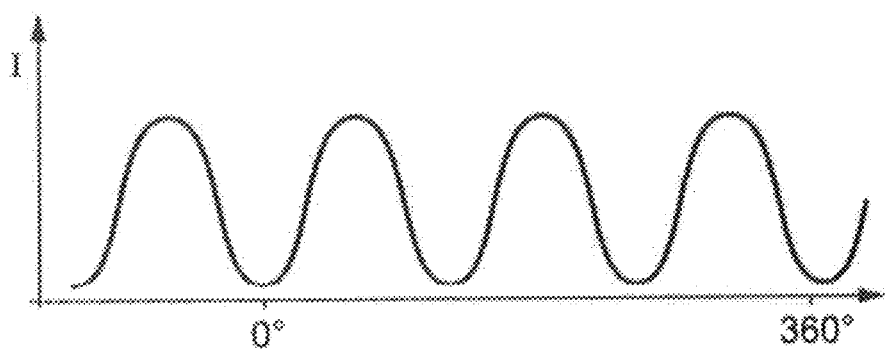

The corresponding cases for linearly polarized input light are presented with reference to FIG. 3. Here FIG. 3A shows, in the four sub-figures lying adjacent to one another, in each case at the top the linearly polarized input polarization state, underneath that the rotational position of the λ/4 plate, underneath that the polarization of the beam after passage through the λ/4 plate, and underneath that those polarization components which the analyzer (polarization beam splitter) transmits to the sensor. It can be discerned that the intensity distribution for linearly polarized light is repeated as early as after a 90° rotation of the λ/4 retardation element, thus resulting in the four-wave undulation of the signal as shown schematically in FIG. 3B.

Figure 4A:
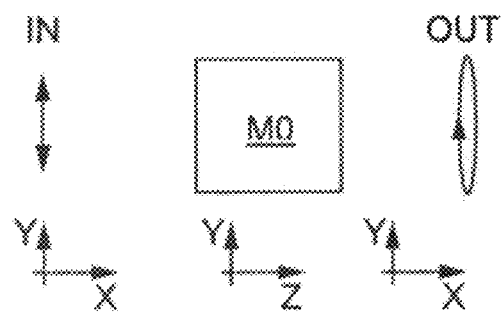
FIG. 4 shows in 4A to 4C schematic illustrations of the dependence of the output polarization state on an input polarization state if a birefringent measurement object is situated in the measurement beam path, in 4D schematic illustrations of different output polarization states in the case of an identical input polarization state as a function of the rotational position of the λ/4 plate, and in 4E a schematic illustration of polarization states within the measurement system in the case of different rotational positions of a non-ideal λ/2 plate for setting the input polarization state.
Figure 4B:
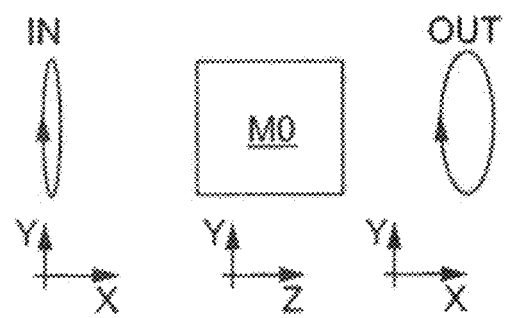

With reference to FIG. 4, further-reaching considerations will now be explained, showing various situations in which a birefringent measurement object MO is situated in the measurement beam path. In this case, the figures schematically elucidate the arising and changing of a two-wave portion in the measurement signal generated by the detector, depending on the input polarization of the measurement beam which enters into the measurement object. In this respect, FIG. 4A shows an idealized case where the input polarization IN is perfectly linear. This can be achieved for example by using a crystal polarizer (e.g. Rochon prism). The birefringence of the measurement object MO leads to a slightly elliptical output polarization state OUT. In accordance with the circumstance that fully circularly polarized light produces a purely two-wave measurement signal, while fully linearly polarized light produces a purely four-wave measurement signal, a measurement signal having a relatively strong four-wave portion (resulting from the linear input polarization) and relative to that a weak two-wave portion (resulting from the slight ellipticity of the polarization state on account of the birefringence of the measurement object) arises for the case of a slightly elliptical output polarization.

If the input radiation is not fully linearly polarized (FIGS. 4B, 4C) because, by way of example, the polarization rotator R1 does not generate a perfect λ/2 retardation, a more highly elliptically polarized polarization state than in the case of FIG. 4A arises in the case of the output polarization OUT after passage through the birefringent measurement object, with the result that the measurement signal once again consists of a strong four-wave portion and relative to that a weak two-wave portion, which, however, is stronger than in the case of ideally linear input polarization (FIG. 4A).

Under these circumstances, at a first position of the λ/2 plate (e.g. +45° relative to an x-axis of a coordinate system of the measurement system) in the case of input polarization in this x-direction downstream of the λ/2 plate and upstream of the measurement object, e.g. slightly right elliptically polarized light ensues. By contrast, if the λ/2 plate is rotated to −45°, then once again elliptically polarized light is generated, which, however, is left circularly polarized in this case (cf. FIG. 4D, where the elliptically polarized states are designated by OUT).

Figure 4C:
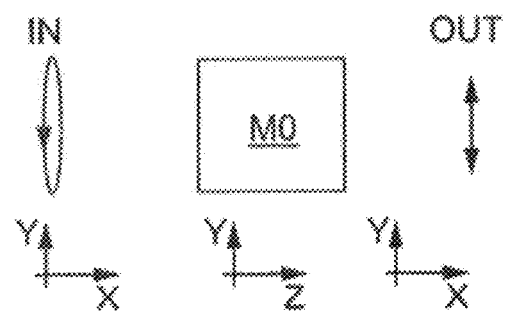

In the first-mentioned case, the ellipticities of the λ/2 plate and of the birefringent measurement object ought to mutually reinforce one another to form more highly elliptically polarized light (FIG. 4B), whereas they at least partly mutually compensate for one another in the other case (other rotational position of the λ/2 plate), such that the output polarization state is closer to an ideally linearly polarized state (FIG. 4C).

The two-wave portion in the measurement signal that is detected by the detector unit is thus stronger in the case of ideally linearly polarized input polarization (FIG. 4A) than in the case of slightly elliptical input polarization (FIGS. 4B, 4C), and from this it can be seen that the absolute value or the value of the two-wave undulation as a function of the rotational position of the λ/2 plate of the beam generating unit is repeated after 180°. It follows from this in turn that the actually sought information about the birefringence of the measurement object resides in the two-wave undulation of the two-wave undulation of the measurement signal.

In order to explain this even further, FIG. 4E shows a representation which illustrates that a possible erroneous retardations (retardation error) of the rotatable λ/2 plate used for setting the input polarization does not generate two-wave undulation in the A2 signal, but rather one-wave undulation, such that, on the basis of the analysis of the two-wave undulation, it is possible to distinguish whether a contribution originates from the measurement object or from the λ/2 plate associated with the measurement system. The representation in FIG. 4E represents the relations in the case of a measurement system without a measurement object, in which the linear polarization (designation IN) of the light source is altered by rotation of a real (i.e. affected by errors) λ/2 plate in order to generate an output polarization state (OUT). The rotational position of the λ/2 plate is symbolized by differently oriented lines. The sub-figures show from left to right different rotational positions and associated nominal output polarization states between 0° and 360°. In accordance with the sub-figure on the left, the output polarization state for 0° results from the fact that the polarization direction of the incident beam runs parallel to the optical crystal axis OA of the λ/2 plate, such that no retardation effect arises. With increasing inclination of the optical crystal axis, the output polarization state, on account of the erroneous retardation of the λ/2 plate, is not exactly linear, but rather slightly elliptical, which can be seen in the case of the output polarization states at 45° and 90°. At the 90° position of the λ/2 plate, a linearly polarized output polarization state is again present, which is rotated by 180° relative to the first position shown on the left. Upon further rotation of the λ/2 plate, elliptically polarized output polarization states then occur again symmetrically to the 180° situation, but they have an opposite chirality relative to the polarization state between 0° and 180°. In the notation introduced in this application, a reversal of the chirality of the polarization is expressed as a change of sign in the two-wave undulation signal A2. On account of the change in the chirality at 180° (that is to say change between right elliptically polarized and left elliptically polarized), a one-wave undulation, that is to say a repetition of the same values of A2 with a period of 360°, arises in the A2 signal illustrated at the bottom (which represents the two-wave undulation). By contrast, the birefringence of a measurement object disposed downstream generates a two-wave undulation in the two-wave undulation because the measurement object turns into itself after a 180° rotation (180° symmetry).

An explanation is given below, by way of example, of the way in which this insight can be utilized for the precise measurement of, in particular, small absolute values of birefringence in embodiments of the invention.

The measurement system is designed to modulate the input polarization state of the measurement beam into at least four different measurement states in accordance with a periodic modulation function of an angle parameter α, to process the polarization measurement values associated with the at least four measurement states to form a measurement function dependent on the angle parameter α, to determine a two-wave portion of said measurement function, and then to analyze said two-wave portion in order to derive the at least one birefringence parameter.

In the case of the example, the input polarization state is generated by virtue of the fact that the measurement light source LS generates a linearly polarized measurement beam and the polarization direction of the measurement beam is altered with the aid of the first polarization rotator R1 by rotation of the polarization rotator between the measurements, such that different measurement orientations of the linear input polarization are present for the measurements. In this case, the angle parameter α corresponds to the rotation angle of the first polarization rotator R1 with respect to a reference direction. The measurement function is derived from the electrical output signal of the sensor SENS and, therefore, in the configuration of the detector unit DET, is proportional to the intensity of the measurement radiation impinging on the sensor, that is to say can be designated as an intensity signal.

The measurement method and the measurement system are designed to determine the values for the birefringence of the measurement object from a Fourier transformation of the two-wave portion of the measurement signal of the sensor, which changes depending on the rotation angle of the first polarization rotator R1. This involves measuring the two-wave portion A2($\alpha$), B2($\alpha$) as a function of the set orientation a of the polarization upstream of the measurement object and then Fourier-transforming it into a with the aid of a fast Fourier transformation (FFT).

In order to be able to use the fast Fourier transformation (FFT), which is favourable with regard to the computational time, upstream of the measurement object $2^N$ (where N≧2) linearly polarized measurement states at equidistant rotation angle distances ($360°/2^N$) are set and the polarization of the output state is measured with the aid of the detector unit.

An explanation is given below of the way in which the birefringent properties of the measurement object, in particular the absolute value of the birefringence and the orientation of the birefringence, can be determined from the measurement signal of the detector unit. The following parameters are used throughout in the representations below:

The configuration of the measurement system for individual measurements is parameterized by way of the following parameters:
PL4: rotation angle of the $\lambda/4$ retardation plate in the detector unit
$\alpha$: measurement orientation of the linear polarization of the measurement beam before entry into the measurement object (set by the first polarization rotator R1).

The variables sought are:
PRdb: absolute value of the birefringence of the measurement object
PRa: orientation of the birefringence of the measurement object (the analyzer of the detector unit (e.g. polarization being splitter) defining the coordinate system for the reference direction).

The disturbances in the measurement system are described by the following parameters:
Lldb: absolute value of the birefringence in the lens group L upstream of the $\lambda/4$ plate of the detector unit
Lla: orientation of the birefringence in the lens group L upstream of the $\lambda/4$ plate of the detector unit
PTdb: absolute value of the birefringence in the analyzer of the detector unit (polarization beam splitter)
PTa: orientation of the birefringence in the analyzer of the detector unit
Tsp: extinction ratio of the analyzer of the detector unit, that is to say the ratio of the transmissions Ts and Tp for s- and p-polarization, respectively, at the beam splitter surface of the polarization beam splitter. The smaller the value of Tsp, the more effective the analyzer.
L4z: erroneous retardation of the $\lambda/4$ plate in the detector unit.

Furthermore, disturbances in the setting of the input polarization can occur, and these are parameterized by:
L2z: erroneous retardation of the first polarization rotator ($\lambda/2$ plate) for setting differently oriented linear polarization states before entry into the measurement object, correspondingly error in the orientation of the linear polarization upstream of the measurement object, parameterized by rotation angle $\alpha$.

One variant of the measurement method then adopts a procedure according to the following measurement specification:

Upstream of the measurement object $2^N$ linearly polarized states (measurement orientations) at equidistant rotation angle distances ($360°/2^N$) are set for a series of measurements. By way of example, it is possible to set eight linear polarization states in accordance with the following orientations: −135°, −90°, −45°, 0°, 45°, 90°, 135°, 180°.

The measurement signals associated with these individual input polarization states at the detector produce a measurement function dependent on the rotation angle $\alpha$, which measurement function is processed in the evaluation unit in order to determine a two-wave portion of the measurement function and then to analyze said two-wave portion. For this purpose, a first Fourier transformation of the measurement function is carried out in order to determine first Fourier coefficients A0($\alpha$) and A2($\alpha$). In this case, the A coefficients designated by "A" are sine portions of the measurement function and the B coefficients designated by "B" are cosine portions of the measurement function. In this case, the coefficient A0($\alpha$) describes an offset term corresponding to an average value of non-periodic portions of the measurement function, while the coefficient A2($\alpha$) is a first two-wave undulation coefficient, which is proportional to the amplitude of the two-wave portion of the measurement function.

Afterwards, the data sets A0($\alpha$) and A2($\alpha$) are Fourier-transformed again with respect to the rotation angle parameter $\alpha$. In other words, a double Fourier transformation of the periodic measurement function takes place. A second Fourier coefficient A0_A01($\alpha$) is calculated from the Fourier transformation of A0($\alpha$). Second Fourier coefficients A2_A02($\alpha$) and B2_A02($\alpha$) are calculated from the Fourier transformation of A2($\alpha$). In this description, A0_A01($\alpha$) denotes an offset term describing an average value of non-periodic portions of the offset term A0($\alpha$), A2_A02($\alpha$) denotes a sine portion of the two-wave undulation of the first two-wave undulation coefficient A2($\alpha$), and B2_A02($\alpha$) denotes a cosine portion of the two-wave undulation of the first two-wave undulation coefficient A2($\alpha$).

In general, the B2($\alpha$) coefficient is also Fourier-transformed again, namely if the $\lambda/4$ plate in the detector unit has a different start value. B2 is =0 only when the optical crystal axis of the $\lambda/4$ plate is parallel or perpendicular to the transmission direction of the polarizer in the start position.

For clarification, the following should also be mentioned: in this embodiment, the first Fourier transformation relates to the parameter pL4, which describes the rotation angle or the rotational position of the $\lambda/4$ retardation plate in the detector unit. This first Fourier transformation is performed for each measurement orientation under consideration (parameterized by angle parameter $\alpha$, set by rotation of the $\lambda/2$ plate (first polarization rotator)). The second Fourier transformation is only carried out by way of the results of the first Fourier transformation as a function of $\alpha$, that is to say for the two-wave portion of $\alpha$. The Fourier coefficients A0($\alpha$) etc. are the results of the first Fourier transformation at the respective location $\alpha$. In the embodiment, therefore, the first Fourier transformation takes place in the detector unit, whereas the second Fourier transformation takes place outside the detector unit.

If a Taylor expansion up to the first order is also performed, then this form of the double Fourier transformation of the measurement function produces the following result (equations (1) to (3)):

$$A0\_A01 = \frac{1}{2} + \frac{1}{2}T_{SP}$$

$$A2\_A02 = -PR_{db}\cos(PR_a)^2 + \frac{1}{2}PR_{db} - Ll_{db}\cos(Ll_a)^2 + \frac{1}{2}Ll_{db}$$

$$B2\_A02 =$$
$$\cos(PT_a)\sin(PT_a)PT_{db} + PR_{db}\cos(PR_a)\sin(PR_a) + Ll_{db}\cos(Ll_a)\sin(Ll_a)$$

The second Fourier transformation of the offset term $A0(\alpha)$ gives rise to the offset term $A0\_A01$, which can be used for an intensity normalization of the measurement result. The second Fourier transformation of the two-wave coefficient $A2(\alpha)$ gives rise to the two-wave portion $A2\_A02$ and $B2\_A02$, which contains the information sought about the birefringence of the measurement object.

It can be seen from equations (1) to (3) that when the measurement is carried out and evaluated in this way, the results for the second Fourier coefficients are not dependent on the erroneous retardations of the $\lambda/2$ plate (first polarization rotator)—used for setting the input polarization—and the $\lambda/4$ plate of the detector unit. This shows that the measurement method is insensitive to these errors of the measurement system to the first order, whereby the accuracy for the measurement values actually sought (birefringence of the measurement object) is increased.

Furthermore, it is evident that the two-wave portions are in each case assembled additively and with exactly identical expressions from the variables to measure ($PR_{db}$ and $PR_a$) and the disturbance variables ($Ll_{db}$, $Ll_a$, $PT_{db}$, $PT_a$) present in the measurement system. Especially the last-mentioned aspect simplifies, during the analysis, separation between the sought birefringence parameters ($PT_{db}$ and $PT_a$), describing the absolute value and the orientation of the birefringence of the measurement object, and the disturbance variables resulting from possible polarization-altering properties of optical elements of the detector unit, specifically as a result of the birefringence of the lens group L and of the polarization beam splitter BS, because in this case it is possible to determine the contribution of the measurement system to the measurement result, the so-called measurement system portion or measurement device offset, using measurements without a measurement object and thus with exactly the same measurement method. In other words: from carrying out a measurement series according to the above-indicated measurement specification for the birefringence of the measurement object, but without a measurement object in the measurement beam path, the disturbing birefringence contributions of the measurement system can be determined and thereby taken into account in the analysis. This is possible by normalizing the two-wave coefficients $A2\_A20$ and $B2\_B20$ to the offset term $A0\_A01$ and subtracting the previously determined and analogously normalized device portions therefrom. In this case, the following apply (equations (4) and (5)):

$$(A2Mn - A2Gn)\left(\frac{1}{2} + \frac{1}{2}T_{sp}\right) = -PR_{db}\cos(PR_a)^2 + \frac{1}{2}PR_{db}$$

$$(B2Mn - B2Gn)\left(\frac{1}{2} + \frac{1}{2}T_{sp}\right) = PR_{db}\cos(PR_a)\sin(PR_a)$$

In this case, $A2Mn=A2\_A02/A0\_A01$ designates the normalized measurement value from the combination of measurement systems and measurement object, and $A2Gn=A2\_A02/A0\_A01$ designates the normalized measurement values from the measurement without a measurement object, that is to say the normalized measurement values of the measurement system alone, that is to say where $PRdb=0$.

If, moreover, the left-hand side of above equation (4) is designated by "A" and the left-hand side of equation (5) below the latter is designated by "B", then the following (equations (6) and (7)) apply for the birefringence parameters $PRdb$ and $PRa$ sought:

$$PR_{db} = 2\sqrt{A^2 + B^2}$$

$$PR_a = -\arctan\left(\frac{B\left(\frac{A^2 + B^2 + \sqrt{A^4 + A^2B^2}}{B^2 + A^2} - 1\right)(B^2 + A^2)}{A(A^2 + B^2 + \sqrt{A^4 + A^2B^2})}\right)$$

Double the absolute value of the two-wave undulation thus directly yields the sought birefringence of the measurement object. The orientation of the birefringence follows from the arc tangent of the B/A ratio.

The novel measurement method has an extremely high measurement accuracy, in particular for relatively small birefringences, which can lie for example in the range of 10 nm or less, or 5 nm or less. It is possible to achieve measurement accuracies of 0.5 nm or less, in particular of 0.4 nm or less or 0.3 nm or less.

Measurement objects having larger birefringence, e.g. having values in the range of significantly more than 10 nm or more than 20 nm or more than 50 nm or more, can be measured with high precision by supplying a birefringence offset, e.g. by introducing a plane plate or a curved plate with known birefringence into the measurement beam path. In this case, the birefringence of the plane plate or of the curved plate is chosen such that a global retardation is brought about for the entire measurement beam, with the result that only relatively small and hence readily measurable residual birefringence values remain, which are then determined.

The following estimations of the measurement accuracy demonstrate the high precision of the measurements. For the estimation of the expected measurement accuracy of the measurement method, measurements were simulated and the deviation between measured and predetermined birefringence values of a measurement object were evaluated. The following typical values were assumed for the measurement system:

Setting of the linear polarization upstream of the measurement object with the aid of a $\lambda/2$ plate with a retardation error of 3 nm. A normally distributed error of the positioning of ±0.5° was assumed with regard to the exactness of the erroneous angle positioning of the polarization rotator. A measurement series with eight measurement orientations of the input polarization that were equidistant in the rotation angle space $\alpha$ was assumed. A retardation error of the $\lambda/4$ plate of the detector unit was fixed at 3 nm, a birefringence contribution of the lens group L upstream of the $\lambda/4$ plate was fixed at 0.5 nm, a birefringence contribution of the analyzer (polarization beam splitter) was fixed at 1 nm, and the extinction ratio of the analyzer was fixed at 0.3%. On the beam generating side, a normally distributed noise of the laser signal with a $\sigma$ value of 0.5% was assumed and the number of support points per polarization measurement was 64 in the case of a 360° rotation.

Figure 5:
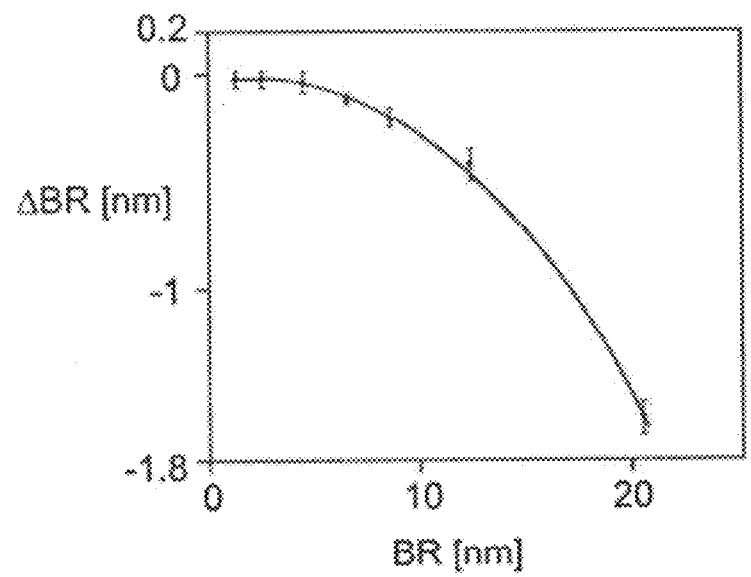
FIG. 5 shows a diagram of the dependence of the average expected deviation ΔBR of the birefringence from a desired value as a function of the absolute value BR of the birefringence in the case of 0° orientation of the birefringence.

In a first step of a simulated measurement, the system portion (measurement device offset) was determined from five measurements to give an average value. Afterwards, the birefringence to be measured was predetermined in a second step, before a simulation of 20 individual measurements and the statistical evaluation thereof were carried out in a third step. The results are explained with reference to FIGS. 5 to 7. FIG. 5 shows a measure of an average measurement error (that is to say for the quality of the measurement methods) for the absolute value of the birefringence in the case of 0° orientation, wherein the predetermined birefringence BR of the measurement object in nanometers is indicated on the x-axis and the average measured or expected deviation ΔBR from the desired value in nanometers is indicated on the y-axis. The offset of the deviation increases to a first approximation quadratically with rising birefringence value. The fluctuation of the measurement value (1σ) is relatively constant independently of the predetermined birefringence and amounts to approximately 0.05 nm. The quadratic increase of the offset is not governed by any principle, but rather results essentially from the fact that the expansion was effected only up to the first order in the case of the evaluation explained above. The offset can be correspondingly reduced in the case of refined analysis.

Figure 6:
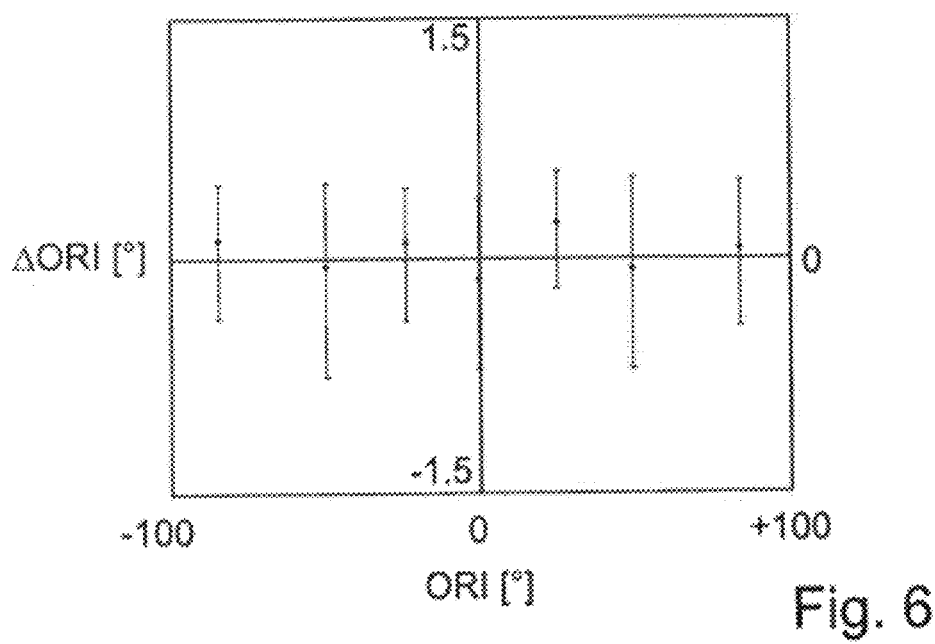
FIG. 6 shows a diagram of the average expected measurement error ΔORI for the orientation of the birefringence in the case of an absolute value of the birefringence of 4 nm as a function of a predetermined orientation of the birefringence.

FIG. 6 shows the average expected measurement errors (that is to say the quality of the measurement method) for the orientation of the birefringence in the case of an absolute value of the birefringence of 4 nm. The predetermined orientation ORI of the birefringence in degrees is indicated on the x-axis, and the y-axis shows the average measured deviation ΔORI from the desired value in degrees. The graph shows impressively that on average the orientation is determined correctly, the orientation error (1σ) being approximately 0.6°.

Figure 7:
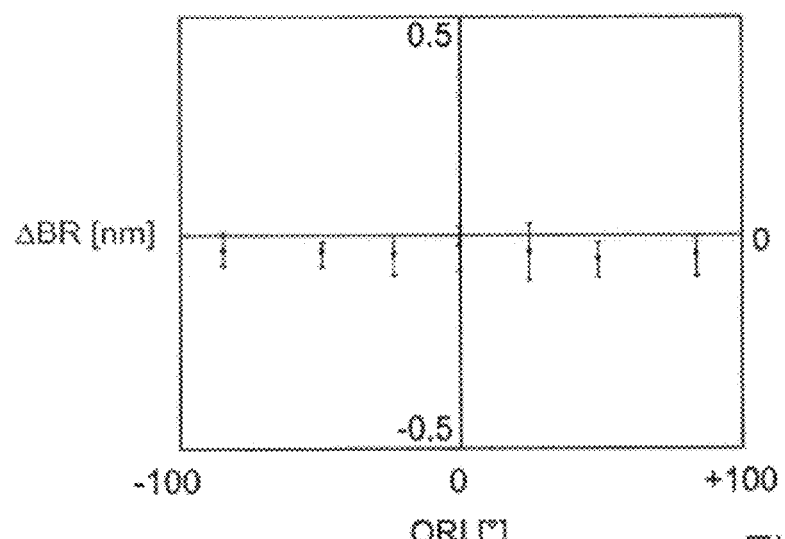
FIG. 7 shows a diagram of the dependence of an average expected deviation ΔBR of the birefringence from a desired value on the orientation ORI of the birefringence of the sample.

FIG. 7 essentially shows that the result of the determination of the absolute value of the birefringence is not dependent on the orientation. In FIG. 7, the average measured or simulated deviation ΔBR from a desired value in nanometers is plotted against the predetermined orientation ORI of the birefringence of the sample in degrees, where 4 nm was assumed for the absolute value of the birefringence.

The simulation show that, in the case of typical errors within a detector unit and in the case of the setting of the input polarization, it is possible to achieve a measurement accuracy of approximately 0.1 nm (1σ) for the absolute value of the birefringence (in the case of absolute values of the birefringence of less than 5 nm) and an orientation error of ±0.6° for the orientation of the birefringence.

A major advantage of the measurement method is that this measurement method to a first approximation does not react to errors which result from the retardation element for setting the input polarization upstream of the measurement object, and so a retardation element that is perfect with regard to the retardation achieved is not required in order nevertheless to obtain highly precise measurement results with a small error. Moreover, the measurement method is insensitive to errors introduced by possible birefringence contributions of the lens or lens group L of the detector unit. By comparison, other measurement methods, wherein such birefringence contributions influence possible measurement errors, generally require a greater direction-dependent correction of the measurement errors if measurement light bundles with a relatively large beam angle range are used for the measurement.

Figures 8A, 8B:
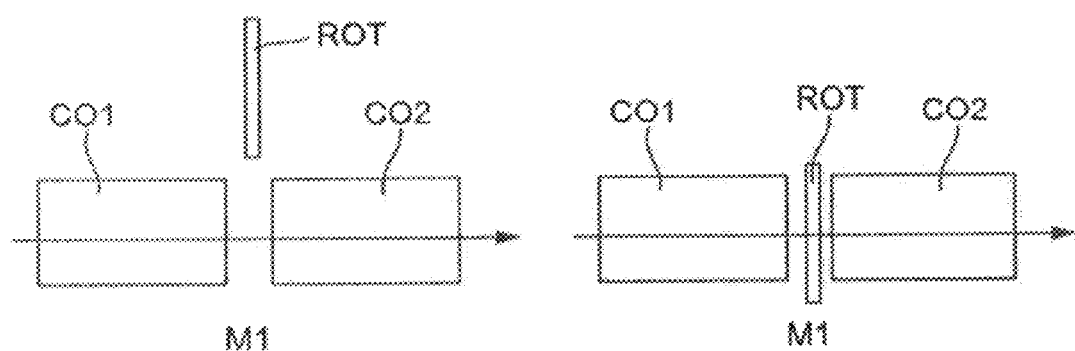
FIG. 8 schematically shows two measurement configurations of a measurement method for measuring measurement objects with two optical components connected in series, wherein a rotation of the polarization state by 90° is performed between the optical components during one of the measurements relative to the other measurement.

An embodiment of the measurement method explained with reference to FIG. 8 makes it possible, in the case of measurement objects which are constructed from a plurality of optical components connected in series, to carry out a separate measurement of the birefringence of the individual components in a small number of measurement cycles, without having to carry out separate measurements on the individual components for this purpose. Rather, the components can remain in an arrangement assembled ready for operation.

In this method variant, two measurement cycles are carried out successively, wherein the measurement system is used in different measurement configurations. In a first measurement, which is identified hereinafter by the abbreviation "M1" in the case of the corresponding parameters and in FIG. 8, the measurement beam, as already described above, is guided through the first optical component and then through the second optical component, the polarization states of the measurement beam not being altered between the optical components. The first measurement thus corresponds to the above-described measurement of the measurement object MO in FIG. 1.

For a second measurement (FIG. 8B), a 90° polarization rotator ROT is introduced into the measurement beam path between the optical components CO1, CO2. In the case of the measurement system in FIG. 1, for this purpose the 90° polarization rotator R3 is introduced between the components CO1 and CO2 by the assigned control device CR3. During the second measurement, the polarization state of the measurement beam is thereby rotated by 90° after passage through the first optical component and before entry into the second optical component. The order of the first and the second measurements can be as described or reversed. The parameters for the second measurement are identified hereinafter by the abbreviation "M2".

After the conclusion of the two measurements, the measurement functions thereby obtained are jointly evaluated. In principle, each of the measurements can be carried out according to the same measurement specification that has already been described above. In particular, for each of the measurements, it is possible to set in each case $2^N$ linearly polarized input polarization states at equidistant rotation angle distances, for example eight linear polarization states. The first Fourier coefficients $A0\_M1(\alpha)$, $A0\_M2(\alpha)$, $A2\_M1(\alpha)$, $A2\_M2(\alpha)$ are determined therefrom in a manner analogous to that described above.

The following equations (8) to (10) then hold true for the first measurement:

$$A0\_A01\_M1 = \frac{1}{2} + \frac{1}{2}T_{sp}$$

$$A2\_A02\_M1 = -FI_{db}\cos(FI_a)^2 + \frac{1}{2}FI_{db} -$$

$$B2\_A02\_M1 = FI_{db}\cos(FI_a)\sin(FI_a) + PT_{db}\sin(PT_a)\cos(PT_a) + FLG_{db}\cos(FLG_a)^2 + \frac{1}{2}FLG_{db} - LI_{db}\cos(LI_a)^2 + \frac{1}{2}LI_{db}$$

$$FLG_{db}\cos(FLG_a)\sin(FLG_a) + LI_{db}\cos(LI_a)\sin(LI_a)$$

By contrast, the following equations (11) to (13) hold true for the second measurement:

$$A0\_A01\_M2 = \frac{1}{2} + \frac{1}{2}T_{sp}$$

$$A2\_A02\_M2 = -FI_{db}\cos(FI_a)^2 + \frac{1}{2}FI_{db} +$$

-continued $$FLG_{db}\cos(FLG_a)^2 - \frac{1}{2}FLG_{db} + LI_{db}\cos(LI_a)^2 - \frac{1}{2}LI_{db}$$

$$B2\_A02\_M2 = FI_{db}\cos(FI_a)\sin(FI_a) - PT_{db}\sin(PT_a)\cos(PT_a) -$$

$$FLG_{db}\cos(FLG_a)\sin(FLG_a) - LI_{db}\cos(LI_a)\sin(LI_a)$$

The parameters used in the equations correspond to the parameters already used in connection with equations (1) to (7).

If the normalized sin two-wave undulation of the measurement 1 is designated by:

$$A2M1n = A2\_A02\_M1/A0\_A01\_M1$$

the normalized sin two-wave undulation of the measurement 2 is designated by:

$$A2M2n = A2\_A02\_M2/A0\_A01\_M2$$

the normalized cos two-wave undulation of the measurement 1 is designated by:

$$B2M1n = B2\_A02\_M1/A0\_A01\_M1$$

the normalized cos two-wave undulation of the measurement 2 is designated by:

$$B2M2n = B2\_A02\_M2/A0\_A01\_M2$$

then the following set of equations (14) to (17) follow from summation and, respectively, difference formation with regard to the above equations:

$$\left(\frac{1}{2}A2M1n + \frac{1}{2}A2M2n\right)\left(\frac{1}{2} + \frac{1}{2}T_{sp}\right) = -\frac{1}{2}FI_{db}(2\cos(FI_a)^2 - 1)$$

$$\left(\frac{1}{2}B2M1n + \frac{1}{2}B2M2n\right)\left(\frac{1}{2} + \frac{1}{2}T_{sp}\right) = FI_{db}\cos(FI_a)\sin(FI_a)$$

$$\left(\frac{1}{2}A2M1n - \frac{1}{2}A2M2n\right)\left(\frac{1}{2} + \frac{1}{2}T_{sp}\right) =$$

$$-FLG_{db}\cos(FLG_a)^2 + \frac{1}{2}FLG_{db} - LI_{db}\cos(LI_a)^2 + \frac{1}{2}LI_{db}$$

$$\left(\frac{1}{2}B2M1n - \frac{1}{2}B2M2n\right)\left(\frac{1}{2} + \frac{1}{2}T_{sp}\right) = PT_{db}\sin(PT_a)\cos(PT_a) +$$

$$FLG_{db}\cos(FLG_a)\sin(FLG_a) + LI_{db}\cos(LI_a)\sin(LI_a)$$

The following is evident from these equations. The sum of the two-wave undulations of the first measurement and of the second measurement contains only the information about the birefringence of the first optical component CO1. The portion of the second optical components and also the system portion originating from the measurement system vanish to a first approximation. That can be understood clearly since the birefringence contributions of the second component CO2 and the system portion contribute to the measurement result with specific signs in the case of the first measurement, while they influence the measurement result with opposite signs in the case of the second measurement, comprising the 90° rotation of the polarization state between first and second optical components, and so they vanish to a first approximation in the course of the summation.

By contrast, the difference between the two-wave undulations of the first measurement and of the second measurement contains only the birefringence portions of the first component CO1 and of the measurement system. That, too, is evidently clear because the contribution both of the first component CO1 and of the overall system to the measurement result is not changed by the introduction of the 90° polarization rotator R3 during the second measurement and thus vanishes in the course of the difference formation.

Since the formulae and equations (14) to (17) have the same structure as the corresponding equations (4) to (7), and the two optical components CO1 and CO2 produce a separate pair of equations, the solution for the birefringence parameters (absolute value and orientation of the birefringence) can be found in an analogous manner to that already described.

It should be mentioned here as a particular advantage that the portion of the first optical component CO1 can be determined without prior calibration of the system portion since, in the course of the summation, the system portion vanishes (apart from the contribution of the extinction ratio Tsp of the analyzer, which can in turn be determined readily and precisely using a separate measurement).

Employing this principle, it is now also evident that it is possible to carry out a (apart from the contribution of the extinction ratio Tsp of the analyzer) calibration-free measurement of the overall system (first optical component CO1 and second optical component CO2) by carrying out a 90° rotation of the polarization state directly upstream of the detector unit between two measurements. In this way, it is possible to carry out an indirect calibration directly at the measurement system without additional structures.

In practice, this can be achieved by providing, for the detector unit DET, an upstream auxiliary optical element that makes it possible to introduce a further 90° polarization rotator for the measurement radiation before entry into the detector unit. For reasons of simplification, FIG. 1 only illustrates the 90° polarization rotator R4 (third polarization rotator), which can optionally be introduced into the measurement beam path or removed from the measurement beam path between the measurement object and the detector unit with the aid of the assigned control device CR4. Provided that the third polarization rotator is integrated into an upstream auxiliary optical element for the detector unit in changeable fashion to allow it to be introduced or removed, either it is possible for measurement to be effected using said upstream auxiliary optical element throughout or it is possible to introduce said upstream auxiliary optical element into the measurement beam path only for the purpose of calibrating the measurement system portion.

A measurement procedure for a measurement-system-independent measurement—i.e. measurement which to the first order is not dependent on errors of the measurement system—of small birefringence contributions of a multicomponent measurement object is described below with reference to FIGS. 9 to 11. For this purpose, FIGS. 9 to 11 schematically show the measurement object MO, which comprises two optical components or modules CO1 and CO2 arranged at a distance one behind the other in the transmission direction (arrow), and also parts of the measurement system that are of particular interest here, namely the detector unit DET, the upstream auxiliary optical element OP fitted between measurement object and detector unit and having the 90° polarization rotator R4, which can optionally be introduced into the measurement beam path or removed therefrom, and also the second polarization rotator R3, which can optionally be introduced between the components CO1 and CO2 or be removed from there.

Figure 9:
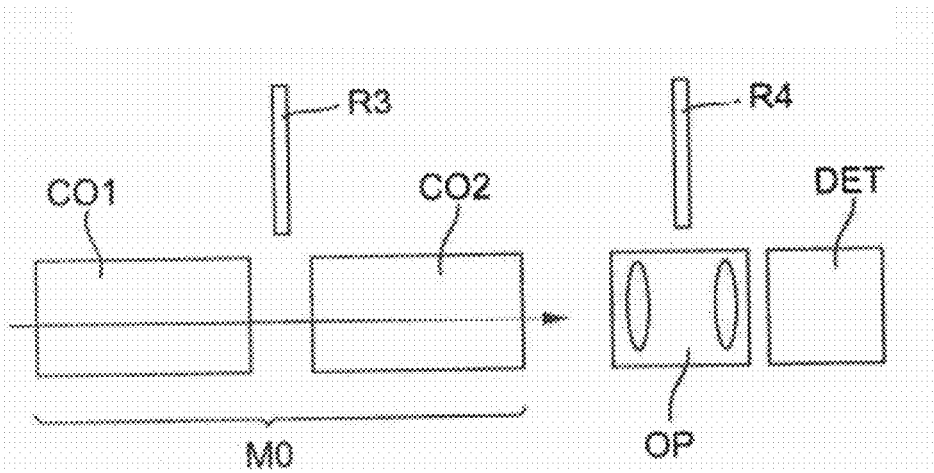
FIGS. 9 to 11 show different measurement configurations of a measurement procedure for a measurement—which is substantially not dependent on errors of the measurement system—of small birefringence contributions of a multicomponent measurement object using 90° polarization rotators that can optionally be inserted into the measurement beam path.

FIG. 9 shows the measurement configuration for a first measurement without the 90° polarization rotator in the region between the components CO1, CO2 and without the 90° polarization rotator in the upstream auxiliary optical element. $2^N$ different input polarization states of the linear input polarization which lie at equidistant rotation angle distances (for example 45°) with respect to one another are set with the aid of the λ/2 plate between measurement light source and measurement object.

Figure 10:
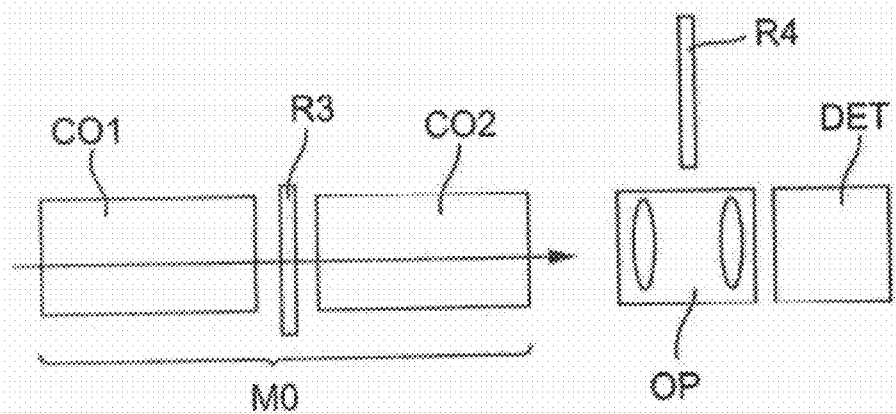
Figure 11:
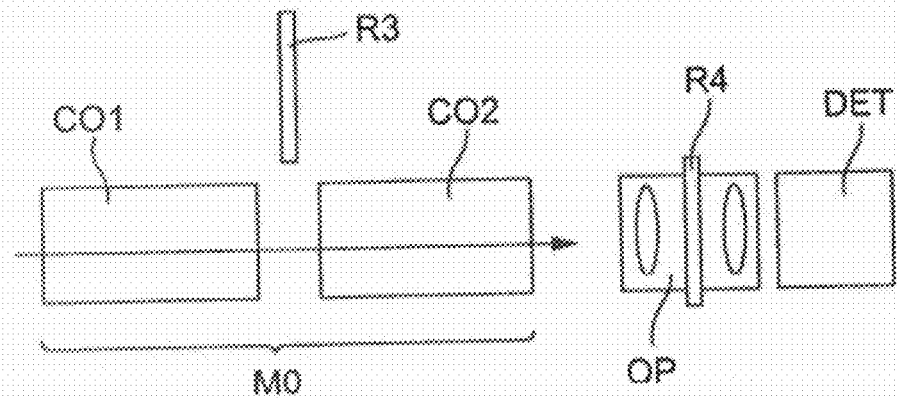

During the second measurement, which is shown in FIG. 10, the 90° polarization rotator R3 is situated in the measurement beam path between the first component CO1 and the second component CO2, while the 90° polarization rotator of the upstream auxiliary optical element is still withdrawn from the measurement beam path. In this case, too, a number of input polarization states corresponding to the first measurement is set and the measurement signal is determined for each polarization state.

During the third measurement, which is illustrated in FIG. 10 and which, in the present case, is utilized only for device calibration, that is to say for calibrating the measurement system, the second polarization rotator R3 is outside the measurement beam path, while the third 90° polarization rotator R4 is arranged within the upstream auxiliary optical element in the measurement beam path.

The birefringence distribution (CO1$db$, CO1$a$) in the first component CO1 is obtained from the first measurement and the second measurement by summation. The following equations (18) and (19) hold true for this:

$$\left(\frac{1}{2}A2M1n + \frac{1}{2}A2M2n\right)\left(\frac{1}{2} + \frac{1}{2}T_{sp}\right) = -\frac{1}{2}CO1_{db}(2\cos(CO1_a)^2 - 1)$$

$$\left(\frac{1}{2}B2M1n + \frac{1}{2}B2M2n\right)\left(\frac{1}{2} + \frac{1}{2}T_{sp}\right) = CO1_{db}\cos(CO1_a)\sin(CO1_a)$$

If the left-hand side of the upper equation (18) is designated by A12 and the left-hand side of the lower equation (19) is designated by B12, then the solution can be derived directly from equations (6) to (7) (see above) by PRdb=CO1$db$, Prr=CO1$a$, A=A12 and B=B12 being equated there.

The measurement system portion, that is to say the portion of the measurement device, is obtained from the first measurement M1 and the third measurement M3 by difference formation, wherein the following equations (20) to (21) and definitions (22) and (23) hold true:

$$\left(\frac{1}{2}A2M1n - \frac{1}{2}A2M2n\right)\left(\frac{1}{2} + \frac{1}{2}T_{sp}\right) = -\frac{1}{2}LI_{db}(2\cos(LI_a)^2 - 1)$$

$$\left(\frac{1}{2}B2M1n - \frac{1}{2}B2M2n\right)\left(\frac{1}{2} + \frac{1}{2}T_{sp}\right) =$$
$$PT_{db}\sin(PT_a)\cos(PT_a) + LI_{db}\cos(LI_a)\sin(LI_a)$$

$$A23nG = \left(\frac{1}{2}A2M1n - \frac{1}{2}A2M3n\right)\left(\frac{1}{2}T_{sp} + \frac{1}{2}\right)$$

$$B23nG = \left(\frac{1}{2}B2M1n - \frac{1}{2}B2M3n\right)\left(\frac{1}{2}T_{sp} + \frac{1}{2}\right)$$

The birefringence distribution in the second optical component CO2 is furthermore obtained from formation of the difference between the first measurement M1 and the second measurement M2 after subtraction of the measurement device portion just determined, in accordance with the following equations (24), (25):

$$\left(\frac{1}{2}A2M1n - \frac{1}{2}A2M2n\right)\left(\frac{1}{2} + \frac{1}{2}T_{sp}\right) =$$

-continued
$$-CO2_{db}\cos(CO2_a)^2 + \frac{1}{2}CO2_{db} - LI_{db}\cos(LI_a)^2 + \frac{1}{2}LI_{db}$$

$$\left(\frac{1}{2}B2M1n - \frac{1}{2}B2M2n\right)\left(\frac{1}{2} + \frac{1}{2}T_{sp}\right) = PT_{db}\sin(PT_a)\cos(PT_a) +$$
$$CO2_{db}\cos(CO2_a)\sin(CO2_a) + LI_{db}\cos(LI_a)\sin(LI_a)$$

The following apply after subtraction of the device portion A23mG and B23mG (equations (26) and (27)):

$$\left(\frac{1}{2}A2M1n - \frac{1}{2}A2M2n\right)\left(\frac{1}{2} + \frac{1}{2}T_{sp}\right) - A23nG =$$
$$-CO2_{db}\cos(CO2_a)^2 + \frac{1}{2}CO2_{db}$$

$$\left(\frac{1}{2}B2M1n - \frac{1}{2}B2M2n\right)\left(\frac{1}{2} + \frac{1}{2}T_{sp}\right) - B23nG = CO2_{db}\cos(CO2_a)\sin(CO2_a)$$

These equations (26) to (27) exhibit a form analogous to that above and can therefore be solved with respect to CO2$db$, CO2$a$.

If, in turn, the left-hand side of the first equation (26) is designated by A12_and the left-hand side of the second equation (27) is designated by B13_, then the solution can be derived directly from equations (6) and (7) by A=13_and B=B13_being equated there.

Since both the first optical component CO1 and the detector unit cause only one offset of the birefringence parameters, all three measurements are required only in the centre of the measurement field.

For all other field points within a field to be measured, the birefringence distribution of the second component CO2 is determined from the second measurement M2, together with the results of the first measurement M1 and the third measurement M3 from the field centre.

Further exemplary embodiments and applications in connection with the measurement of the birefringence in components and subsystems of a projection exposure apparatus for microlithography are explained below.

Figure 12:
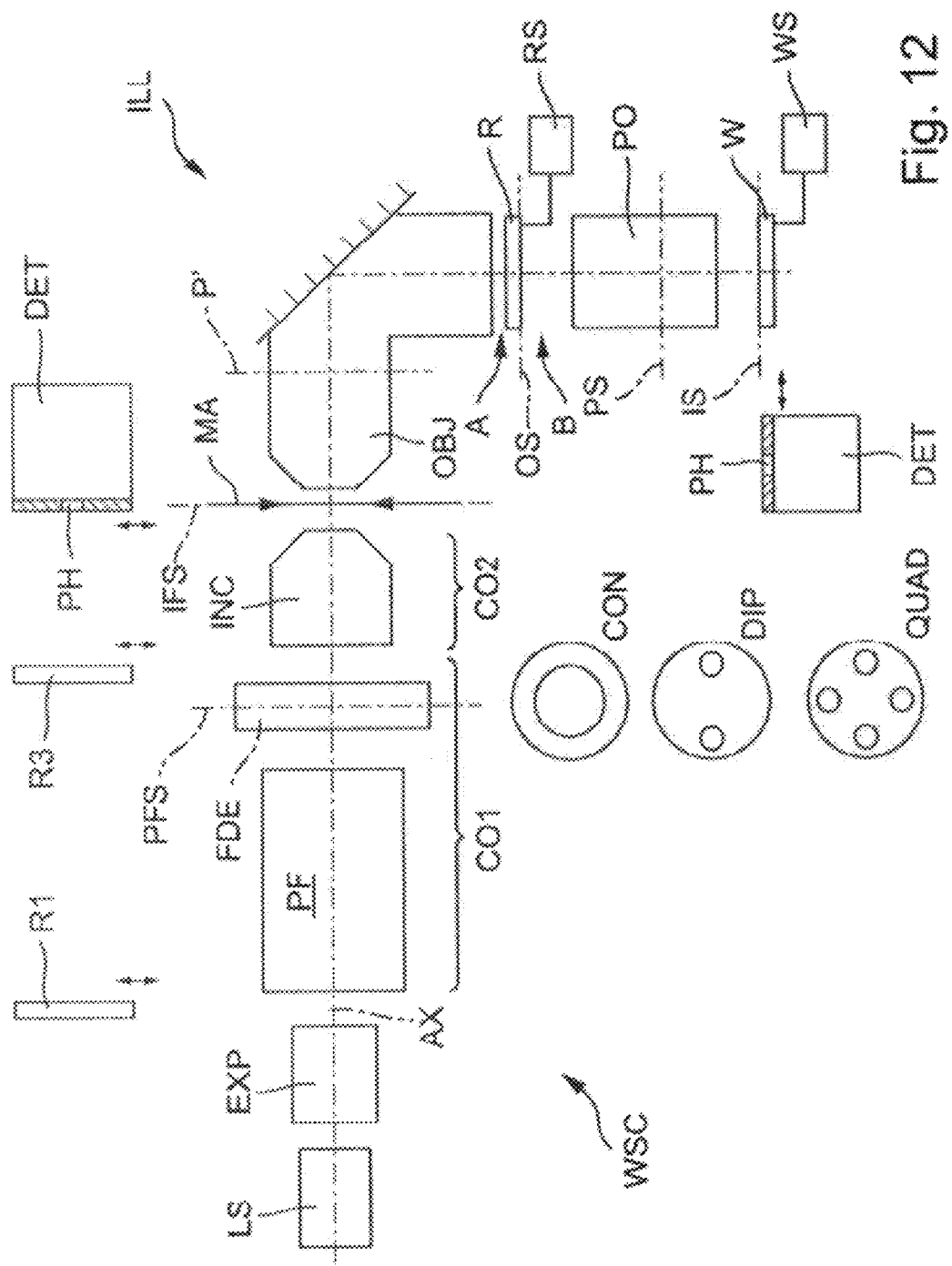
FIG. 12 shows an embodiment of a microlithography projection exposure apparatus with components of an integrated measurement system for measuring the birefringence.

FIG. 12 shows an example of a microlithography projection exposure apparatus WSC which can be used in the production of semiconductor components and other finely structured components and operates with light or electromagnetic radiation from the deep ultraviolet range (DUV) in order to obtain resolutions down to fractions of micrometers. An ArF excimer laser having an operating wavelength of approximately 193 nm serves as a primary light source LS, the linearly polarized laser beam of said laser being coupled into the illumination system coaxially with respect to the optimal axis AX of the illumination system 190. Other UV laser radiation sources, for example $F_2$ lasers having an operating wavelength of 157 nm, or ArF excimer lasers having an operating wavelength of 248 nm, are likewise possible.

The polarized light from the light source LS firstly enters into a beam expander EXP, which serves for example for reduction of coherence and enlargement of the beam cross section. The expanded laser beam enters into a pupil forming unit PF, which contains a multiplicity of optical components and groups and is designed to generate, in a downstream pupil forming surface PFS of the illumination system ILL, a defined, local (two-dimensional) illumination intensity distribution, which is sometimes also referred to as secondary light source or as "illumination pupil". The pupil forming surface PFS is a pupil surface of the illumination system.

The pupil forming unit PF can be set in variable fashion, such that different local illumination intensity distributions (that is to say differently structured secondary light sources) can be set depending on the driving of the pupil forming unit. Various illuminations of the circular illumination pupil are shown schematically by way of example in FIG. 12, namely a conventional setting CON with a centred, circular illumination spot, a dipole illumination DIP or a quadrupole illumination QUAD.

An optical raster element FDE is arranged in direct proximity to the pupil forming surface PFS. A coupling-in optical element INC arranged downstream of said raster element transfers the light to an intermediate field plane IFP, in which a reticle/masking system MA is arranged, which serves as an adjustable field stop. The optical raster element FDE, which is also referred to as field-defining element, has a two-dimensional arrangement of diffractive or refractive optical elements and shapes the entering radiation such that the latter illuminates a rectangular illumination field after passing through the downstream coupling-in optical element INC in the region of the intermediate field plane IFP. The radiation is additionally homogenized by the superimposition of partial beam bundles, such that the FDE serves as field shaping and homogenizing element.

The downstream imaging objective OBJ (also called REMA objective) images the intermediate field plane IFP with the field stop MA onto the reticle M (mask, lithography original) on a scale which can be between 2:1 and 1:5, for example, and is approximately 1:1 in the embodiment.

Those optical components which receive the light from the laser LS and form illumination radiation from the light, said illumination radiation being directed onto the reticle M, belong to the illumination system ILL of the projection exposure apparatus.

Arranged downstream of the illumination system is a device RS for holding and manipulating the reticle M in such a way that the pattern arranged on the reticle lies in the object plane OS of the projection objective PO and can be moved in said plane for scanner operation in a scanning direction (y-direction) perpendicularly to the optical axis AX (z-direction) with the aid of a scanning drive.

Downstream of the reticle plane OS there follows the projection objective PO, which acts as a reducing objective and images an image of the pattern arranged on the mask M onto a wafer W on a reduced scale, for example on a scale of 1:4 or 1:5, said wafer being coated with a photoresist layer and the light-sensitive surface of said wafer lying in the image plane IS of the projection objective PO. Refractive, catadioptric or catoptric projection objectives are possible. Other reduction scales, for example greater demagnifications up to 1:20 or 1:200, are possible.

The substrate to be exposed, which is a semiconductor wafer W in the case of the example, is held by a device WS comprising a scanner drive in order to move the wafer synchronously with the reticle R perpendicularly to the optical axis. Depending on the design of the projection objective PO (e.g. refractive, catadioptric or catoptric, without intermediate image or with intermediate image, folded or unfolded), these movements can be effected parallel or antiparallel to one another. The device WS, which is also referred to as "wafer stage", and the device RS, which is also referred to as "reticle stage", are part of a scanner device that is controlled by a scanning control device.

The pupil forming surface PFS lies at or near a position which is optically conjugate with respect to the nearest downstream pupil surface P' and with respect to the image-side pupil surface PS of the projection objective PO. Consequently, the spatial (local) light distribution in the pupil PS of the projection objective is determined by the spatial light distribution (spatial distribution) in the pupil forming surface PFS of the illumination system. Lying between the pupil surfaces PFS, P', PS there are in each case field surfaces in the optical beam path, which are Fourier-transformed surfaces relative to the respective pupil surfaces. This means, in particular, that a defined spatial distribution of illumination intensity in the pupil forming surface PFS produces a specific angle distribution of the illumination radiation in the region of the downstream field surface IFS, which in turn corresponds to a specific angle distribution of the illumination radiation incident on the reticle M.

Figure 13A:
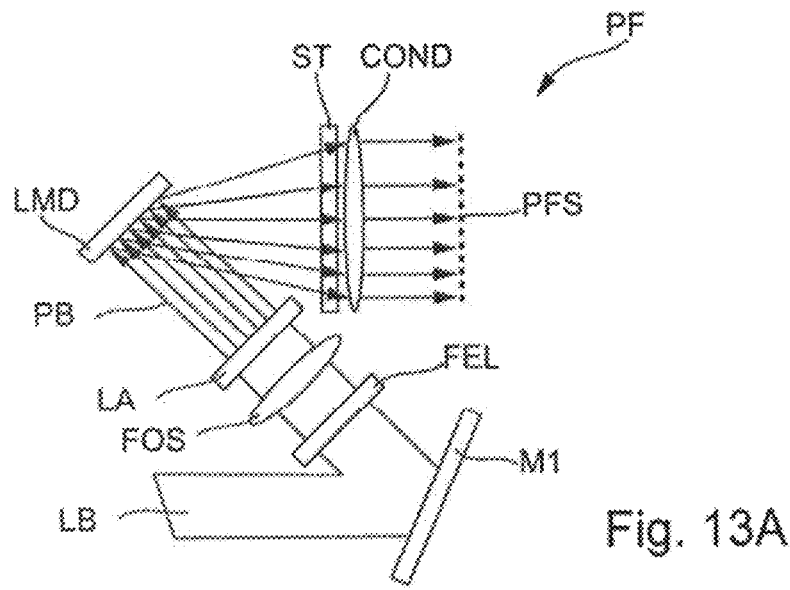
FIG. 13 shows various assemblies of the illumination system of the projection exposure apparatus from FIG. 12.
Figure 13B:
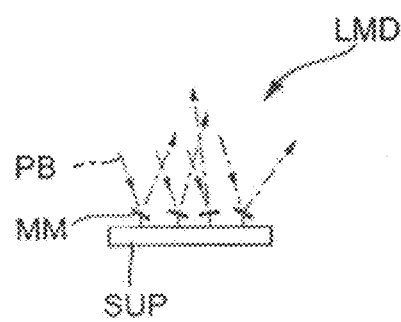
Figure 13C:
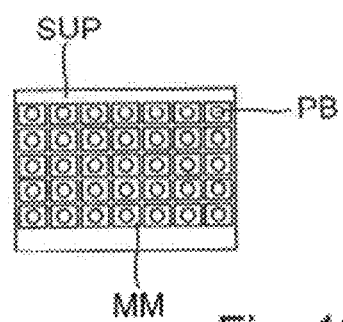

Components of an embodiment of a pupil forming unit PF are shown schematically in FIGS. 13A, B and C. The entering, expanded laser radiation bundle LB is deflected by a plane deflection mirror M1 in the direction of a fly eyes condenser (fly eyes lens) FEL, which decomposes the arriving radiation bundle into partial illumination beam bundles, which are subsequently transferred through a Fourier optical system FOS onto a lens array LA, that is to say onto a two-dimensional array arrangement of lens systems. The lens array LA concentrates the partial illumination beam bundles PB onto individually drivable mirror elements of a multi-mirror arrangement LMD (multi-mirror array, MMA), which is also shown in FIGS. 13B and 13C. The multi-mirror arrangement is operated here as a reflective light modulation device for controllably altering the angle distribution of the radiation bundle incident on the light modulation device and, using the orientation of its individual mirrors MM, provides for an illumination angle distribution which can be defined with the aid of the multi-mirror arrangement and which is superimposed in the pupil forming surface PFS to form an intensity distribution in this pupil surface. The individual mirrors MM of the multi-mirror arrangement, which are fitted to a common support element SUP, can be tilted about one or more axes in order to alter the propagation angle of the impinging partial illumination beam bundles PB. The partial illumination beam bundles issuing from the individual mirrors MM are passed through a diffusing screen ST and imaged into the pupil forming surface PFS using a downstream condenser optical element COND. The lens array LA and/or the micromirror arrangement LMD can essentially be constructed in the manner described in US 2007/0165202 A1 in the name of the present applicant. The disclosure in this regard in said patent application is incorporated by reference in the content of this description. Transmissive light modulation devices are also possible.

One task when producing components of such a projection exposure apparatus may consist, for example, in separately determining the birefringence of the assemblies PF and FDE provided for forming the illumination pupil and the birefringence of the downstream coupling-in group INC, in order, by way of example, through exchange or adjustment of individual elements, to be able to achieve the effect that the birefringence contributions of the overall arrangement do not exceed a predetermined tolerance. For this purpose, the optical components to be measured, in that arrangement in which they are also utilized during operation of the projection exposure apparatus, are installed into a measurement object holder of a birefringence measurement system and are measured in this configuration. In this case, the combination of pupil forming unit PF and field-defining element FDE forms a first optical component CO1, and the coupling-in group arranged at a distance downstream thereof forms a second optical component CO2 (cf. FIG. 1). The light source LS of the test set-up serves as the light source of the measurement system.

The measurement system furthermore comprises a first polarization rotator R1 in the form of a half-wave plate, which is introduced into the beam path between the beam expander EXP and the pupil forming unit PF and which is mounted such that it is rotatable about the optical axis of the illumination system. Furthermore, a second 90° polarization rotator R3 is provided, which can optionally be introduced into the beam path between the first optical component CO1 and the second optical component CO2 or be moved out of this position, with the aid of a changing device. In the case of the measurement arrangement, the detector unit DET of the measurement system is arranged in such a way that the pinhole PH, that is to say the entrance opening of the detector unit, is situated in the intermediate field plane IFS following the coupling-in group. For the calibration described further above, a third 90° polarization rotator R4 can also be provided, which can optionally be introduced into the measurement beam path in the region between the second optical component CO2 and the entrance of the detector unit DET or be removed from said measurement beam path. The measurement set-up can essentially be like that described in connection with FIG. 1, the first optical component CO1 being formed by the combination of pupil forming unit and field-defined element and the second optical component CO2 being formed by the coupling-in group.

As already mentioned, the detector unit enables an angularly resolving polarization measurement with a high angular resolution. Furthermore, the spatial distribution of the intensity in the pupil forming surface is translated, by the coupling-in group acting as a Fourier lens group, into a corresponding angle distribution in the intermediate field plane in which the pinhole PH of the detector unit is situated. As a result, a pupil-resolved birefringence measurement can be carried out with the aid of the measurement set-up. In this respect, reference is made to the description of various measurement methods indicated above.

It is also possible to arrange the detector unit downstream of the imaging objective OBJ, such that the entrance surface of the detector unit is situated in the reticle plane OS. In this case, birefringence contributions of the imaging objective OBJ also influence the measurement and can be determined separately from the contributions of the other components by corresponding positioning of optionally insertable 90° polarization rotators.

Embodiments of the measurement system can also be utilized for measuring birefringence on a projection exposure apparatus assembled ready for operation. In one embodiment, a measurement system is integrated into a projection exposure apparatus. The exemplary embodiment, likewise explained with reference to FIG. 12, has a detector unit DET, which can be arranged, instead of a wafer to be exposed, in the region of the image plane of the projection objective in such a way that the entrance plane of the detector unit with the pinhole is situated in the image plane of the projection objective and can be displaced perpendicularly to the optical axis of the projection objective in order to measure different field points within said plane. With the aid of this integrated measurement system it is now possible, for example, to detect metrologically the birefringence of a reticle (mask M) during operation of the projection exposure apparatus. A corresponding measurement can take place for example in each case after a reticle change, in order to ensure that the birefringence of the reticle does not exceed an upper limit predetermined for the process and/or in order to obtain a database for the birefringence distribution in order to compensate for the influence of the birefringence of the reticle by corresponding compensation mechanisms.

In principle, the measurement of the birefringence of the reticle installed into the projection exposure apparatus can be carried out analogously to the procedure described in connection with FIGS. 8 to 11. In this case, the reticle which is to be measured with regard to its birefringence corresponds to the second component CO2. For this method, the projection exposure apparatus has two changing devices for optionally inserting or removing 90° polarization rotators from the beam path. A first changing device is designed to insert a first 90° polarization rotator into the space A between the output of the illumination system and the reticle. A second changing device is designed to optionally insert a second 90° polarization rotator into the space B between the reticle and the projection objective. Moreover, the illumination system contains a $\lambda/2$ plate which can optionally be inserted into the illumination beam path and which, in the inserted position, can be rotated about the optical axis of the illumination system in order to set the input polarization states for the measurement (corresponding to the rotatable $\lambda/2$ plate R1 from FIG. 1).

The detector unit can also be modified for the measurement of the birefringence of the reticle in such a way that it does not measure the pupil, but rather the field directly. For this purpose, it can be arranged in such a way that the light distribution of the reticle field is incident on the sensor area (e.g. CCD chip). For this purpose, the sensor area can be arranged e.g. in the image plane of the projection objective, which is optically conjugate with respect to the object plane of the projection objective, in which the reticle to be measured is arranged. A reticle with large surfaces can be scanned in this way, whereby the measurement time can be shortened by comparison with a measurement with scanning of individual field points.

For the birefringence measurement on the reticle, firstly the pupil forming unit PF of the illumination system is set such that a conventional illumination setting with an ultralow degree of coherence is present, such that illumination intensity is present in the pupil forming surface PFS practically only in direct proximity to the optical axis. The degree of coherence $\sigma$ is defined here as the ratio of the output-side numerical aperture of the illumination system to the input-side numerical aperture of the downstream projection objective. The $\sigma$ value can be e.g. less than 0.2 or less than 0.15 or 0.1 or less than 0.1. If appropriate, a pinhole diaphragm may also be inserted in order to obtain a single, quasi point-type secondary light source situated on the optical axis in the pupil forming surface PFS. A measurement beam composed of measurement light that is collimated to the greatest possible extent is generated in this way, said measurement beam being directed onto the reticle. A collimated beam path with substantially perpendicular light incidence on the reticle permits a precise setting of the input polarization state at the reticle since radiation passes through the polarization-optical components used for the setting practically exclusively parallel to the optical axis and, consequently, only very little angle loading and retardation errors associated therewith are present.

For each of the measurements described below, at least four different input polarization states corresponding to different orientations of the linear polarization are generated by rotation of the $\lambda/2$ plate in the illumination system.

A first measurement is carried out without the 90° polarizer in the region A between illumination system and reticle and also without the 90° polarization rotator between reticle and projection objective (region B). $2^N$ different linear input polarization states are set with the aid of the $\lambda/2$ plate in the illumination system.

For a second measurement, the first 90° polarization rotator is inserted into the measurement beam path between illumination system and reticle (region A), while the second 90° polarization rotator, provided for the region B between reticle and projection objective, is still withdrawn from the measurement beam path. In this configuration, too, a number of input polarization states that corresponds to the first measurement is set and the measurement signal is determined for each polarization state.

For a third measurement, the first polarization rotator is removed from the space A between illumination system and reticle and the second 90° polarization rotator is inserted into the space B between reticle and projection objective. In this configuration, too, once again a number of input polarization states that corresponds to the first measurement is set and the measurement signal is determined for each polarization state.

Analogously to the explanations in connection with FIGS. 8 to 11, the birefringence distribution in the components of the illumination system which lie downstream of the $\lambda/2$ plate (corresponding to the first component CO1 there) is obtained from the first measurement and the second measurement by summation. The measurement system portion, that is to say the portion of the measurement system, which also comprises the projection objective PO in the present case, is obtained from the first measurement and the third measurement by difference formation.

Finally, the birefringence distribution in the reticle is obtained from formation of the difference between the first measurement and the second measurement after subtraction of the system portion just determined (measurement device and projection objective).

The measurement accuracy of the measurement method can be impaired by intensity fluctuations of the measurement light used. A possibility for detecting an energy reference and thus for correcting such intensity fluctuation effects is explained below which can be realized with manageable technological outlay in the context of the measurement system. The example of a pupil-resolved polarization measurement of components of the illumination system of a projection exposure apparatus is particularly instructive in this regard. In an illumination system of the type described in connection with FIGS. 12 and 13, the laser light from the primary light source is incident on a multi-mirror array (MMA), the individual mirrors of which are each movable in a small angle range independently of other individual mirrors, such that, through combination of the angular position of the individual mirrors, it is possible to set a desired angle distribution of the reflected radiation and hence a desired spatial distribution in the pupil plane of the illumination system.

One problem during this measurement is that the intensity distribution on the mirrors of the multi-mirror array can fluctuate on a time scale of individual laser pulses and on a length scale of a few micromirrors. The fluctuations can lie e.g. in the range of ±10%. Since, in such a spatially resolving light modulation device, an individual element (micromirror) illuminates only a small part of the pupil, the intensity fluctuation at the multi-mirror array is translated directly into a location-dependent intensity fluctuation in the pupil plane.

Figure 14:
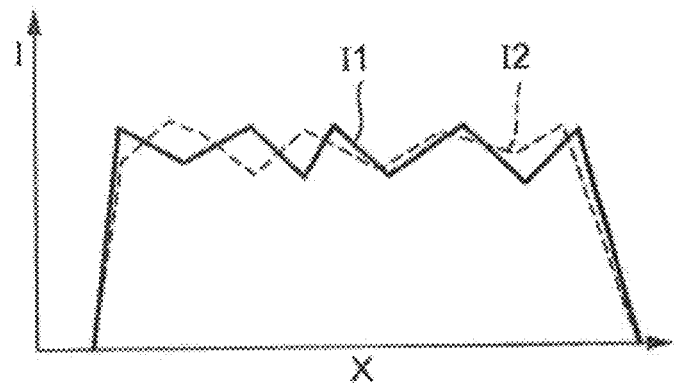
FIG. 14 schematically shows the dependence of the relative intensity I in the pupil surface of an illumination system on the location X at different points in time.

The intensity fluctuation results substantially from fluctuation of the laser profile and the laser angles in combination with intermixing effects in the beam feed and in essence is attributed to self-interference of the coherent laser radiation. FIG. 14 shows by way of example the dependence of the relative intensity I in the pupil surface on the location X on the basis of two different local intensity distributions 11 and 12 that are present at different points in time t1 and t2, respectively.

The following problem thus arises for a pupil-resolved polarization measurement. The measurement of the angle-dependent polarization properties (or of the distribution of the polarization over the pupil) of an illumination system is an intensity measurement of the radiation in a field plane (for example reticle plane or intermediate field plane) using an angularly resolving detector. If the intensity distribution over the pupil changes during the spatially resolving measurement in the pupil, then this means a disturbance of the measurement, which leads to a decrease in the measurement accuracy if the intensity fluctuation is not suitably monitored and taken into account in the evaluation of the polarization measurement.

An energy reference can be created by carrying out a time-dependent detection of a reference intensity signal, which is proportional to the intensity of the measurement light emitted by a measurement light source, and by using a normalization of the polarization measurement signal to the reference intensity signal in order to determine normalized polarization measurement signals.

The generalized principle of one variant of energy referencing is explained with reference to FIG. 15. One essential aspect of this variant consists in splitting the intensity-fluctuating light from the light source into two partial beams polarized perpendicularly to one another with the aid of a birefringent element or some other device for beam splitting in such a way that the two partial beams simultaneously impinge on the same light-sensitive sensor (e.g. CCD chip) at different locations and are recorded jointly during a polarization measurement. The measurement arrangement should preferably be constructed in such a way that the two orthogonally polarized partial beams traverse polarization-optically and/or geometrically similar paths between the splitting location and the impinging location at the sensor through the intervening system. Under these conditions, the partial beams experience an approximately identical change in the polarization as a result of possible polarization-influencing elements in the system, such that they arrive in the detector unit in a manner still polarized approximately orthogonally with respect to one another. Under these assumptions, the sum of the two signals on the sensor area is proportional to the total energy of the light source at each point in time and can therefore be utilized as a reference energy signal.

In this respect, FIG. 15A shows a light source LS which over the course of time t shall have an intensity fluctuation, that is to say a fluctuation of the relative intensity I in accordance with FIG. 15B. In the beam path downstream of the light source there follows a retarder RET, for example a small retardation plate or a polarizer or depolarizer, in order, upstream of a subsequent birefringent element SP, to set the polarization of the radiation such that, downstream of the birefringent element SP, both the ordinary ray O and the extraordinary ray AO carry a quantity of light energy that is suitable for the evaluation. The measurement radiation that has been split in this way then passes through the measurement object MO, which can bring about a change in polarization. Since the paths of the two partial beams through the measurement object are similar, both experience substantially the same relative change in polarization. The measurement object can be for example an illumination system of a projection exposure apparatus or an individual module of such an illumination system or an individual element of an illumination system or of some other optical system. After passing through the measurement object, the two partial beams arrive at the detector unit DET, which can be constructed with a rotatable $\lambda/4$ retardation plate R2 and a polarization beam splitter BS, embodied as a beam splitter cube, and also an area sensor SENS in the manner as described in connection with FIG. 1.

The partial beams impinge on the sensor area directly alongside one another and form in this case a first illumination spot or spot SP1 (e.g. for the ordinary ray) and a second illumination spot or spot SP2 (e.g. for the extraordinary ray). FIG. 15C shows the relative intensities within the spots for different points in time within the measurement time. In this case, the sum of the intensities of the first spot and of the second spot, as is illustrated schematically in FIG. 15C, is substantially proportional to the laser energy fluctuation in accordance with FIG. 15B. The summation signal can thus be utilized as an energy reference for a normalization of the polarization measurement signal.

The functional principle of this particular type of energy referencing can be explained illustratively as follows. The two mutually orthogonal polarization states of the partial beams generated by the splitting produce unpolarized light when summed. Since the detector unit, in response to unpolarized light, independently of the rotational position of the retardation plate, yields a constant signal proportional to the laser energy, the sum of the two partial beam intensities, on account of incoherent summation in the region of the evaluation software, produces a signal which is substantially proportional to the (possibly fluctuating) intensity of the light source.

If the orientation of the birefringent element SP with respect to the coordinate system of the measurement object is known, then it is additionally possible to deduce from the ratio of the two intensities of the first spot SP1 and of the second spot SP2 the polarization portions in the direction of the polarization of the ordinary and the extraordinary ray, respectively. If this information is additionally coupled to the rotational position of the retardation plate R2, then unpolarized and polarized portions of the radiation can also respectively be deduced from the ratio of the intensities at different rotational positions.

In principle, the combination of the retardation element RET (e.g. λ/4 plate) arranged between light source and birefringent element and the birefringent element SP serving for beam splitting is once again a polarization measurement system that can be used to measure the polarization distribution of the radiation coming from the light source. In combination with a spatial assignment, a limited spatially resolved measurement of the polarization distribution is possible. Such a system could be used to detect e.g. the polarization-optical properties of a beam delivery system arranged between the laser light source and the illumination system of a projection exposure apparatus.

Figure 16:
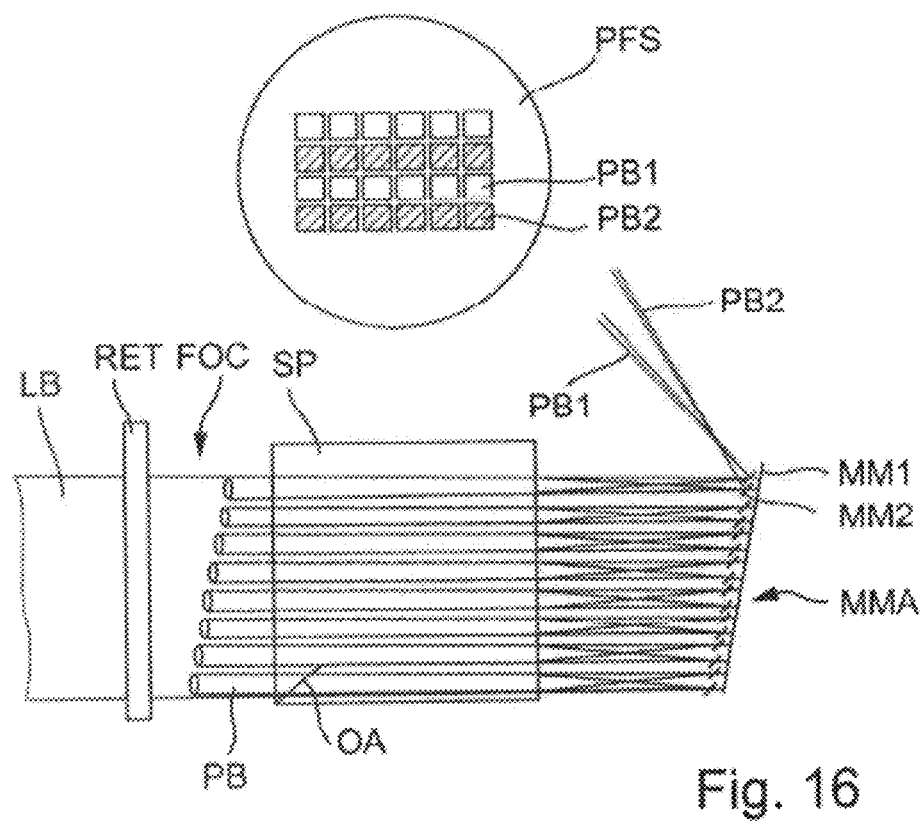
FIG. 16 shows an excerpt from the pupil shaping unit—shown schematically in FIG. 13A—of an illumination system with a birefringent beam splitting element by generating partial beams that are polarized orthogonally in pairs from partial beams of a beam bundle.

With reference to FIG. 16 in combination with FIGS. 12 and 13, an explanation will be given of a possible implementation of such energy referencing in the measurement of components of an illumination system which has a multi-mirror array MMA in its pupil forming unit. In this respect, FIG. 16 shows an excerpt from the pupil forming unit shown schematically in FIG. 13A. This part of the system comprises the multi-mirror array MMA and an upstream lens array FOC, which, as a focussing array, serves to decompose the expanded laser beam into partial beams PB, which then impinge on individual mirrors of the mirror arrangement MMA. A birefringent element SP is introduced into the beam path between focussing array and mirror array. The polarization of the beam impinging on the focussing array is set by a retardation element RET in such a way that, taking account of the orientation of the optical crystal axis OA of the birefringent element SP, the partial beams generated by the focussing array are split into partial beams PB1 and PB2 that are polarized perpendicularly to one another in each case. For the measurement, in each case two adjacent individual mirrors MM1, MM2 are then set such that two partial beams PB1, PB2 having orthogonal polarization are respectively imaged directly alongside one another in the pupil forming surface PFS. When summed in pairs, the intensities of these partial beams yield the information sought about the intensity fluctuation of the laser LS. In this case, the evaluation is advantageously carried out in such a way that in each case the sum of directly adjacently impinging partial beams having orthogonal polarization is formed since these traverse substantially the same optical paths and also experience substantially the same fluctuation of the intensity.

Since the number of individual lenses or individual optical channels of the focussing array FOC normally corresponds to the number of individual mirrors of the multi-mirror array MMA, in order respectively to concentrate the radiation of an optical channel onto an individual mirror, for the measurement provision is made for using upstream of the focusing array a raster diaphragm which splits the arriving beam in such a way that only every second microlens is utilized for the polarization measurement.

The measurement can be carried out on an illumination system that has already been assembled ready for operation, by virtue of the detector unit DET of the measurement system being arranged with its entrance plane into the reticle plane (exit plane of the illumination system, during operation identical to the object plane of the projection objective). The measurement can then be carried out in the manner already described.

The splitting of the measurement beam into two partial beams polarized perpendicularly to one another, which splitting is provided for the energy referencing, can be carried out with the aid of different beam splitting devices. Thus, a polarization beam splitter can also be used instead of a birefringent element, by way of example. It is also not mandatory for the splitting into partial beams to take place in the light path upstream of the measurement object or within the measurement object. Rather, the splitting into orthogonally polarized partial beams can also be performed after passage through the measurement object, in particular also within the detector unit. Some examples in this respect are explained below in connection with FIGS. 17 and 18.

Figure 17A:
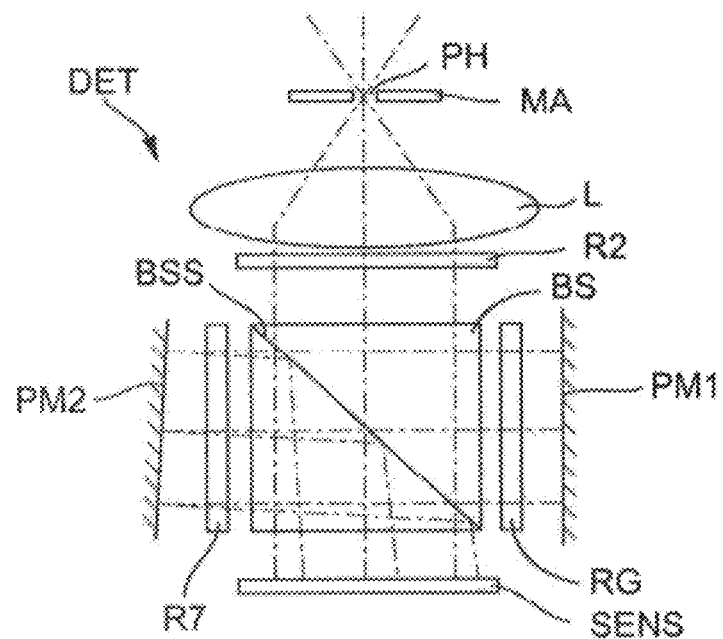
FIG. 17 shows in 17A schematically the construction of a detector unit of a polarization measurement system with an integrated beam splitting element for generating two partial beams polarized orthogonally with respect to one another for energy referencing, and in 17B and 17C different arrangements of the illumination spots of partial beams polarized perpendicularly to one another, said illumination spots being directly adjacent to one another.
Figure 17B:
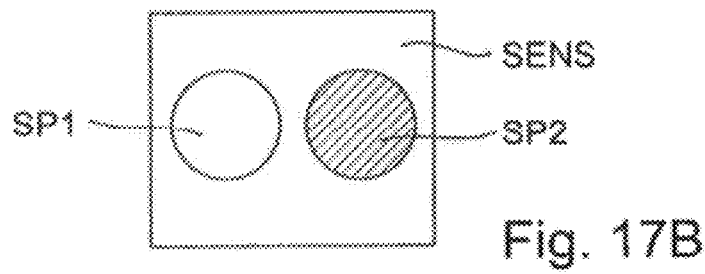
Figure 17C:
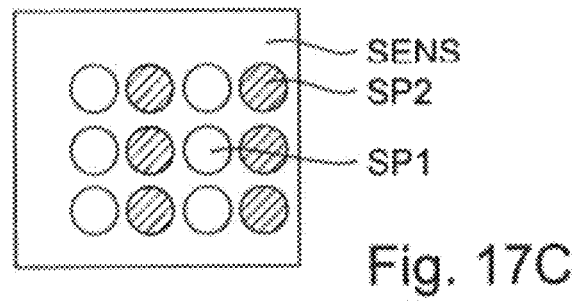

FIG. 17A shows a schematic illustration of a detector unit DET for a polarization measurement system that can be used to measure the birefringence of optical elements, components or systems. The basic components of the detector unit, in particular the mask M having the entrance opening (pinhole PH), the lens L, the rotatable retardation element RT, the polarization beam splitter BS (analyzer) and the sensor (SENS), correspond to the correspondingly designated components of the embodiment from FIG. 1, for which reason reference is made to the description in respect thereof.

In addition, at that side of the beam splitter BS at which the radiation reflected from the beam splitter surface firstly emerges, there are arranged a λ/4 plate R6 and a highly reflective plane mirror PM1, the mirror surface of which is perpendicular to the optical axis of the detector unit, said optical axis being folded at the beam splitter surface BSS. At the opposite side of the beam splitter, a further λ/4 retardation plate R7 is provided, and so is a further highly reflective plane mirror PM2, the planar mirror surface of which is tilted slightly in the direction of the sensor relative to the planar mirror surface of the other plane mirror PM1 or relative to the optical axis.

In this arrangement, the polarization beam splitter BS acts as a beam splitting element which generates two partial beams which are polarized perpendicularly to one another and which impinge on the sensor area of the sensor SENS directly alongside one another. In this case, the function is as follows. Firstly, the measurement beam collimated by the lens L enters into the beam splitter BS and is split by the beam splitter surface BSS into a partial beam having p-polarization (polarization direction parallel to the plane of incidence on the beam splitter surface), which passes through to the sensor SENS, and into an s-polarized partial beam, which is reflected by the beam splitter surface. The reflected partial beam emerges from the polarization beam splitter in the direction of the first plane mirror PM1, acquires circular polarization as a result of the λ/4 plate, is then reflected at the plane mirror and, after repeated passage through the λ/4 plate and hence a total retardation of λ/2, has a polarization direction rotated by 90°, with the result that it is now p-polarized with respect to the beam splitter surface. The p-polarized beam entering into the beam splitter again is then transmitted from the beam splitter surface to the opposite side and emerges from the beam splitter on the opposite side. After passage through the λ/4 plate R7, the now circularly polarized beam is reflected at the inclined plane mirror PM2 in such a way that the reflected beam is inclined slightly in the direction of the sensor relative to the incident beam. After repeated passage through the λ/4 plate R7, s-polarization is then present, such that the beam is then reflected from the beam splitter surface in the direction of the sensor area. The tilting angle of the plane mirror PM2 relative to the direction of incidence of the beam that is directed onto said mirror is dimensioned, then, such that the partial beam directed to the sensor by multiple reflection impinges on the sensor area in a manner laterally offset with respect to the directly transmitted partial beam, alongside the latter.

In the case of this arrangement, although the partial beams after the polarization-selective beam splitting traverse different geometrical paths (one partial beam is transmitted directly to the sensor and the other is reflected multiply at planar mirror surfaces), the beam paths are identical or polarization-optically equivalent in so far as the multiply reflected partial beam experiences as a whole relative to the directly transmitted partial beam only a phase retardation of exactly one wavelength.

In a departure from the schematic illustration in FIG. 17A, it is possible to set the beam diameter of the measurement beam through the illumination system in such a way that the partial beams which impinge on the sensor SENS in a manner laterally offset with respect to one another do not overlap, but rather impinge in a manner offset alongside one another without an overlap. For this purpose, by way of example, with the illumination system, it is possible to generate a greatly underfilled illumination pupil with only one pole situated eccentrically with respect to the optical axis. A situation such as is shown schematically in FIG. 17B can then be established at the sensor area of the sensor SENS. This figure shows on the left the first spot SP1, formed by the partial beam that passes through directly, and on the right the second spot SP2, which is formed by the multiply reflected partial beam.

In a corresponding manner, during the measurement of an illumination system, the measurement beam, with the aid of the multi-mirror array MMA, can be decomposed into a larger number of partial beams in accordance with a finer rastering of the illumination pupil, which then enter into the detector unit and form on the sensor SENS a finer raster of spots SP1, SP2 lying directly alongside one another, in each case one of the spots resulting from the partial beam having s-polarization and the other spot SP2 resulting from the partial beam having the orthogonal polarization relative thereto. During the evaluation, preferably the intensities of spots SP1, SP2 lying directly alongside one another in each case are then evaluated for the energy referencing.

Figure 18:
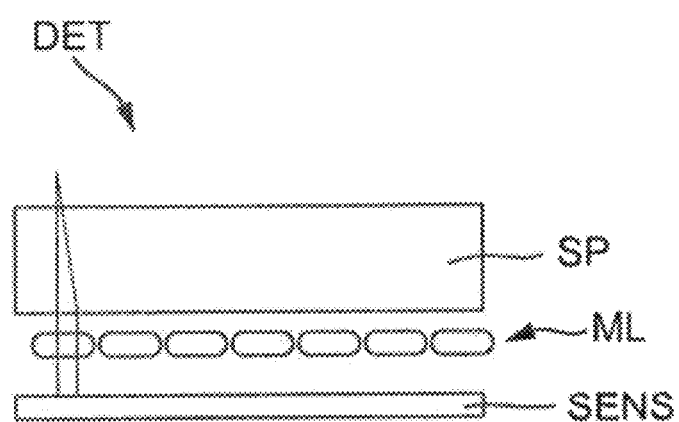
FIG. 18 schematically shows some components of a detector unit with an integrated beam splitting element for generating partial beams polarized perpendicularly to one another for energy referencing.

FIG. 18 shows part of a detector unit DET in which a birefringent beam splitting element SP is arranged upstream of the sensor area SENS. The birefringent element SP splits the radiation directed at the sensor into partial beams polarized perpendicularly to one another, given corresponding orientation of the optical crystal axis of said element, as is shown schematically on the left. A microlens array ML is fitted between the birefringent element and the sensor and splits the beam passing through into a number of partial beams corresponding to the number of illuminated microlenses, and forms on the sensor area for each of the partial beams spots for the two parts of the partial beams that are polarized perpendicularly to one another. In this embodiment, the microlens array ML can perform the function of the rastering of the pupil, such that a measurement is possible even without a multi-mirror array in the measurement object to be measured.

Consequently, on the basis of a few exemplary embodiments, a description has been given here of a method for the spatially resolved measurement of the change in the polarization distribution by an optical system in which a beam splitting of the measurement beam into two partial beams polarized orthogonally with respect to one another is effected in such a way that the two partial beams impinge on the sensor—acting in spatially resolving fashion—of the measurement system at adjacent locations.

The above description of various embodiments has been given by way of example. From the disclosure given, those skilled in the art will not only understand the present invention and its attendant advantages, but will also find apparent various changes and modifications to the structures and methods disclosed. The applicant seeks, therefore, to cover all such changes and modifications as fall within the spirit and scope of the invention, as defined by the appended claims, and equivalents thereof.

The invention claimed is:

1. A measurement system for measuring birefringence of an optical measurement object comprising:
   a beam generating unit configured to generate a measurement beam having a defined input polarization state, the measurement beam being directed onto the measurement object;
   a detector unit configured to detect polarization properties of the measurement beam after interaction with the measurement object and to generate polarization measurement values representing an output polarization state of the measurement beam; and
   an evaluation unit configured to evaluate the polarization measurement values and to determine at least one birefringence parameter representing the birefringence of the measurement object,
      wherein the beam generating unit is further configured to modulate the input polarization state of the measurement beam into at least four different measurement states in accordance with a periodic modulation function of an angle parameter α; and
      wherein the evaluation unit is further configured to process the polarization measurement values associated with the at least four measurement states, to form a measurement function dependent on the angle parameter α, to determine a two-wave portion of the measurement function and to analyze the two-wave portion, in order to derive the at least one birefringence parameter.

2. The measurement system according to claim 1, wherein the beam generating unit comprises, between a light source configured to generate linearly polarized light and the measurement object, a first polarization rotator configured to be controlled to rotate a polarization direction of the measurement beam.

3. The measurement system according to claim 2, wherein the first polarization rotator comprises a half-wave plate, which is configured to rotate about an optical axis of the measurement system under control of a first control device.

4. The measurement system according to claim 2, comprising a second polarization rotator configured as a 90° polarization rotator that rotates the polarization state of the measurement beam by 90° and which is configured to be introduced into and removed from the measurement beam path under control of a second control device.

5. The measurement system according to claim 4, wherein the second polarization rotator is arranged in proximity to a measurement object holding device and is configured to be introduced into and removed from a region between a first optical component and a second optical component of the measurement object, the measurement object comprising a plurality of optical components.

6. The measurement system according to claim 4, comprising a third polarization rotator configured as a 90° polarization rotator that rotates the polarization state of the measurement beam by 90° and which is configured to be introduced into and removed from the measurement beam path in a region between the measurement object and the detector unit under control of a third control device.

7. The measurement system according to claim 4, wherein the 90° polarization rotator is selected from the group consisting of:
   a plate composed of optically active material;
   a plate composed of intrinsically birefringent crystal material having a crystallographic <110> direction oriented substantially parallel to a transmission direction of the measurement beam; and
   two low-order half-wave plates oriented at 45° relative to one another, wherein optical crystal axes of the half-wave plates rotated relative to one another are substantially perpendicular to the transmission direction.

8. The measurement system according to claim 1, wherein the detector unit has an entrance opening configured to displace to predetermined positions in a plane perpendicularly to the optical axis of the measurement system.

9. The measurement system according to claim 1, wherein the detector unit is designed for an angularly resolving measurement of the polarization state.

10. A projection exposure apparatus for exposing a radiation-sensitive substrate arranged proximate to an image surface of a projection objective with at least one image of a pattern of a mask arranged proximate to an object surface of the projection objective, comprising:
   a primary light source configured to emit primary light;
   an illumination system configured to receive the primary light and to generate an illumination beam directed onto the mask;
   a projection objective configured to generate an image of the pattern proximate to the image surface of the projection objective; and
   a measurement system configured to measure the birefringence of an optical measurement object arranged between the primary light source and the image surface of the projection objective, the measurement system comprising:
      a beam generating unit configured to generate a measurement beam having a defined input polarization state, the measurement beam being directed onto the measurement object;
      a detector unit configured to receive the measurement beam after interaction with the measurement object and to generate polarization measurement values representing an output polarization state of the measurement beam; and
      an evaluation unit configured to evaluate the polarization measurement values and to determine at least one birefringence parameter representing the birefringence of the measurement object.

11. The projection exposure apparatus according to claim 10, wherein the primary light source of the projection exposure apparatus is comprised within the beam generating unit that generates the measurement beam directed onto the measurement object.

12. The projection exposure apparatus according to claim 10, wherein the detector unit is positioned, in lieu of a substrate to be exposed, in proximity to the image plane of the projection objective such that an entrance plane of the detector unit with an entrance opening is situated in the image surface of the projection objective or in an optically conjugate surface with respect to the image surface of the projection objective.

13. The projection exposure apparatus according to claim 12, wherein the entrance opening is configured to displace perpendicularly to the optical axis of the projection objective, to measure different field points within the image surface.

14. The projection exposure apparatus according to claim 10, wherein the detector unit is positioned, in lieu of a mask, proximate to the object surface of the projection object such that an entrance plane of the detector unit with an entrance opening is situated in the object surface of the projection objective or in an optically conjugate surface with respect to the object surface of the projection objective.

15. The projection exposure apparatus according to claim 10, wherein the measurement system is configured to carry out a measurement method comprising:
   generating a measurement beam having a defined input polarization state, the measurement beam being directed onto the measurement object, the input polarization state being the polarization state of the measurement beam directly before the measurement beam enters into the measurement object;
   detecting polarization properties of the measurement beam after interaction with the measurement object, to generate polarization measurement values representing an output polarization state of the measurement beam after interaction with the measurement object;
   evaluating the polarization measurement values, to determine at least one birefringence parameter representing the birefringence of the measurement object,
   modulating the input polarization state of the measurement beam into at least four different measurement states in accordance with a periodic modulation function of an angle parameter $\alpha$;
   processing the polarization measurement values associated with the at least four measurement states, to form a measurement function dependent on the angle parameter $\alpha$;
   determining a two-wave portion of the measurement function; and
   analyzing the two-wave portion, to derive the at least one birefringence parameter.

16. A measurement method for measuring birefringence of a reticle, comprising:

arranging the reticle in an installation position between an illumination system and a projection objective of a projection exposure apparatus proximate to an object surface of the projection objective; and measuring the birefringence of the reticle in the installation position with a measurement system for measuring the birefringence of an optical measurement object, wherein the measurement system is integrated into the projection apparatus;

wherein said measuring comprises:

generating a measurement beam having a defined input polarization state, the measurement beam being directed onto the reticle, the input polarization state being the polarization state of the measurement beam directly before the measurement beam enters into the reticle;

detecting polarization properties of the measurement beam after interaction with the reticle in order to generate polarization measurement values representing an output polarization state of the measurement beam after interaction with the reticle; and evaluating the polarization measurement values, to determine at least one birefringence parameter representing the birefringence of the reticle.

17. The measurement method according to claim 16, further comprising performing the measurement after a reticle change and before an exposure using the reticle introduced by the change.

18. The measurement method according to claim 16, wherein said measuring further comprises:

modulating the input polarization state of the measurement beam into at least four different measurement states in accordance with a periodic modulation function of an angle parameter $\alpha$;

processing the polarization measurement values associated with the at least four measurement states, to form a measurement function dependent on the angle parameter $\alpha$;

determining a two-wave portion of the measurement function; and analyzing the two-wave portion, to derive the at least one birefringence parameter.

19. The measurement system according to claim 1, comprising a polarization rotator configured as a 90° polarization rotator that rotates the polarization state of the measurement beam by 90° and which is configured to be introduced into and removed from the measurement beam path under control of a control device.

20. The measurement system according to claim 1, comprising a polarization rotator configured as a 90° polarization rotator that rotates the polarization state of the measurement beam by 90° and which is configured to be introduced into and removed from the measurement beam path in a region between the measurement object and the detector unit under control of a control device.

* * * * *

UNITED STATES PATENT AND TRADEMARK OFFICE
CERTIFICATE OF CORRECTION

PATENT NO. : 8,542,356 B2
APPLICATION NO. : 13/237000
DATED : September 24, 2013
INVENTOR(S) : Damian Fiolka and Marc Rohe It is certified that error appears in the above-identified patent and that said Letters Patent is hereby corrected as shown below:

In the Specification

Column 19, line 14: delete "a of" and insert -- $\alpha$ of -- therefor.

Signed and Sealed this
Twenty-second Day of April, 2014

Michelle K. Lee
*Deputy Director of the United States Patent and Trademark Office*